United States Patent
Lee et al.

(10) Patent No.: US 7,668,591 B2
(45) Date of Patent: Feb. 23, 2010

(54) AUTOMATIC ACTIVATION OF MEDICAL PROCESSES

(75) Inventors: Kent Lee, Eridley, MN (US); Jeffrey E. Stahmann, Ramsey, MN (US); Jesse W. Hartley, Lino Lakes, MN (US); Quan Ni, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 872 days.

(21) Appl. No.: 10/922,663

(22) Filed: Aug. 20, 2004

(65) Prior Publication Data

US 2005/0081847 A1 Apr. 21, 2005

Related U.S. Application Data

(60) Provisional application No. 60/504,381, filed on Sep. 18, 2003.

(51) Int. Cl.
*A61B 5/04* (2006.01)

(52) U.S. Cl. .................. 600/544; 600/546; 607/2; 607/6

(58) Field of Classification Search ............... 600/300, 600/301, 529, 544, 545, 546; 607/2, 6
See application file for complete search history.

(56) References Cited

U.S. PATENT DOCUMENTS

| | | |
|---|---|---|
| 4,365,636 A | 12/1982 | Barker |
| 4,562,841 A | 1/1986 | Brockway et al. |
| 4,813,427 A | 3/1989 | Schlaefke et al. |
| 4,827,935 A | 5/1989 | Geddes et al. |
| 4,830,008 A | 5/1989 | Meer |
| 4,928,688 A | 5/1990 | Mower |
| 5,036,849 A | 8/1991 | Hauck et al. |
| 5,105,354 A | 4/1992 | Nishimura |
| 5,123,425 A | 6/1992 | Shannon, Jr. et al. |

(Continued)

FOREIGN PATENT DOCUMENTS

EP 0940155 9/1999

(Continued)

OTHER PUBLICATIONS

Bradley et al., Pathophysiologic and Therapeutic Implications of Sleep Apnea in Congestive Heart Failure, 3 J. Cardiac Failure 223-240 (1996). Abstract only.

(Continued)

*Primary Examiner*—Max Hindenburg
*Assistant Examiner*—Jonathan M. Foreman
(74) *Attorney, Agent, or Firm*—Hollingsworth & Funk, LLC

(57) ABSTRACT

Systems and methods involve automatic activation, de-activation or modification of therapies or other medical processes based on brain state. A medical system includes a sensor system having one or more sensors configured to sense signals related to the brain state of the patient. A brain state analyzer detects various brain states, including sleep stage and/or brain seizures. A controller uses the brain state detection information to control a medical system configured to perform at least one respiratory or cardiac process. Methods involve sensing signals related to brain state and determining the brain state of a patient based on the sensed signals. At least one respiratory or cardiac medical process is controlled based on the patient's brain state.

20 Claims, 18 Drawing Sheets

U.S. PATENT DOCUMENTS

| | | |
|---|---|---|
| 5,146,918 A | 9/1992 | Kallok et al. |
| 5,178,156 A | 1/1993 | Takishima et al. |
| 5,187,657 A | 2/1993 | Forbes |
| 5,203,348 A | 4/1993 | Dahl et al. |
| 5,211,173 A | 5/1993 | Kallok et al. |
| 5,215,082 A | 6/1993 | Kallok et al. |
| 5,230,337 A | 7/1993 | Dahl et al. |
| 5,233,983 A | 8/1993 | Markowitz |
| 5,284,136 A | 2/1994 | Hauck et al. |
| 5,301,677 A | 4/1994 | Hsung |
| 5,313,953 A | 5/1994 | Yomtov et al. |
| 5,334,222 A | 8/1994 | Salo et al. |
| 5,335,657 A * | 8/1994 | Terry et al. .................. 607/45 |
| 5,353,788 A * | 10/1994 | Miles .................. 128/204.23 |
| 5,360,442 A | 11/1994 | Dahl et al. |
| 5,366,496 A | 11/1994 | Dahl et al. |
| 5,376,476 A | 12/1994 | Eylon |
| 5,388,578 A | 2/1995 | Yomtov et al. |
| 5,391,200 A | 2/1995 | KenKnight et al. |
| 5,397,342 A | 3/1995 | Heil, Jr. et al. |
| 5,411,031 A | 5/1995 | Yomtov |
| 5,466,245 A | 11/1995 | Spinelli et al. |
| 5,483,969 A | 1/1996 | Testerman et al. |
| 5,485,851 A | 1/1996 | Erickson |
| 5,522,862 A | 6/1996 | Testerman et al. |
| 5,540,727 A | 7/1996 | Tockman et al. |
| 5,545,186 A | 8/1996 | Olson et al. |
| 5,545,202 A | 8/1996 | Dahl et al. |
| 5,549,655 A | 8/1996 | Erickson |
| 5,593,431 A | 1/1997 | Sheldon |
| 5,603,732 A | 2/1997 | Dahl et al. |
| 5,645,570 A | 7/1997 | Corbucci |
| 5,738,102 A | 4/1998 | Lemelson |
| 5,836,987 A | 11/1998 | Baumann et al. |
| 5,844,680 A | 12/1998 | Sperling |
| 5,855,593 A | 1/1999 | Olson et al. |
| 5,861,011 A | 1/1999 | Stoop |
| 5,891,023 A | 4/1999 | Lynn |
| 5,911,218 A | 6/1999 | DiMarco |
| 5,916,243 A | 6/1999 | KenKnight et al. |
| 5,944,680 A | 8/1999 | Christopherson et al. |
| 5,964,778 A | 10/1999 | Fugoso et al. |
| 5,964,788 A | 10/1999 | Greenhut |
| 5,974,340 A | 10/1999 | Kadhiresan |
| 5,974,349 A | 10/1999 | Levine |
| 6,026,320 A | 2/2000 | Carlson et al. |
| 6,044,297 A | 3/2000 | Sheldon et al. |
| 6,044,298 A | 3/2000 | Salo et al. |
| 6,055,454 A | 4/2000 | Heemels |
| 6,064,910 A | 5/2000 | Andersson et al. |
| 6,076,015 A | 6/2000 | Hartley et al. |
| 6,091,973 A | 7/2000 | Colla et al. |
| 6,099,479 A | 8/2000 | Christopherson et al. |
| 6,120,441 A | 9/2000 | Griebel |
| 6,126,611 A | 10/2000 | Bourgeois et al. |
| 6,128,534 A | 10/2000 | Park et al. |
| 6,132,384 A | 10/2000 | Christopherson et al. |
| 6,141,581 A | 10/2000 | Olson et al. |
| 6,141,590 A | 10/2000 | Renirie et al. |
| 6,221,011 B1 | 4/2001 | Bardy |
| 6,240,316 B1 | 5/2001 | Richmond et al. |
| 6,251,126 B1 | 6/2001 | Ottenhoff et al. |
| 6,259,947 B1 | 7/2001 | Olson et al. |
| 6,269,269 B1 | 7/2001 | Ottenhoff et al. |
| 6,270,457 B1 | 8/2001 | Bardy |
| 6,272,377 B1 | 8/2001 | Sweeney et al. |
| 6,275,727 B1 | 8/2001 | Hopper et al. |
| 6,277,072 B1 | 8/2001 | Bardy |
| 6,280,380 B1 | 8/2001 | Bardy |
| 6,285,907 B1 | 9/2001 | Kramer et al. |
| 6,312,378 B1 | 11/2001 | Bardy |
| 6,317,627 B1 | 11/2001 | Ennen |
| 6,336,903 B1 | 1/2002 | Bardy |
| 6,351,669 B1 | 2/2002 | Hartley et al. |
| 6,353,759 B1 | 3/2002 | Hartley et al. |
| 6,358,203 B2 | 3/2002 | Bardy |
| 6,363,270 B1 | 3/2002 | Colla et al. |
| 6,368,284 B1 | 4/2002 | Bardy |
| 6,371,922 B1 | 4/2002 | Baumann et al. |
| 6,398,728 B1 | 6/2002 | Bardy |
| 6,409,675 B1 | 6/2002 | Turcott |
| 6,411,848 B2 | 6/2002 | Kramer et al. |
| 6,415,183 B1 | 7/2002 | Scheiner et al. |
| 6,424,865 B1 | 7/2002 | Ding |
| 6,431,171 B1 * | 8/2002 | Burton .................. 128/204.18 |
| 6,438,407 B1 | 8/2002 | Ousdigian et al. |
| 6,438,410 B2 | 8/2002 | Hsu et al. |
| 6,440,066 B1 | 8/2002 | Bardy |
| 6,449,503 B1 | 9/2002 | Hsu |
| 6,459,929 B1 | 10/2002 | Hopper et al. |
| 6,480,733 B1 | 11/2002 | Turcott |
| 6,487,443 B2 | 11/2002 | Olson et al. |
| 6,527,729 B1 | 3/2003 | Turcott |
| 6,542,775 B2 | 4/2003 | Ding et al. |
| 6,574,507 B1 | 6/2003 | Bonnet |
| 6,589,188 B1 | 7/2003 | Street et al. |
| 6,597,951 B2 | 7/2003 | Kramer et al. |
| 6,600,949 B1 | 7/2003 | Turcott |
| 6,641,542 B2 | 11/2003 | Cho et al. |
| 6,658,292 B2 | 12/2003 | Kroll et al. |
| 6,741,885 B1 | 5/2004 | Park et al. |
| 6,752,765 B1 | 6/2004 | Jensen et al. |
| 6,773,404 B2 | 8/2004 | Poezevera et al. |
| 2001/0018547 A1 | 8/2001 | Mechlenburg et al. |
| 2002/0193697 A1 | 12/2002 | Cho et al. |
| 2002/0193839 A1 | 12/2002 | Cho et al. |
| 2003/0023184 A1 | 1/2003 | Pitts-Crick et al. |
| 2003/0055461 A1 | 3/2003 | Girouard et al. |
| 2003/0100925 A1 | 5/2003 | Pape et al. |
| 2003/0153953 A1 | 8/2003 | Park et al. |
| 2003/0153954 A1 | 8/2003 | Park et al. |
| 2003/0153955 A1 | 8/2003 | Park et al. |
| 2003/0153956 A1 | 8/2003 | Park et al. |
| 2003/0163059 A1 | 8/2003 | Poezevera et al. |
| 2003/0195571 A1 | 10/2003 | Burnes et al. |
| 2003/0199945 A1 | 10/2003 | Ciulla |
| 2003/0204213 A1 | 10/2003 | Jensen et al. |
| 2003/0216789 A1 * | 11/2003 | Deem et al. .................. 607/9 |
| 2004/0002742 A1 | 1/2004 | Florio |
| 2004/0030362 A1 | 2/2004 | Hill et al. |
| 2004/0059240 A1 | 3/2004 | Cho et al. |
| 2004/0088027 A1 | 5/2004 | Burnes et al. |
| 2004/0133079 A1 | 7/2004 | Mazar et al. |
| 2004/0138719 A1 | 7/2004 | Cho et al. |
| 2004/0176809 A1 | 9/2004 | Cho et al. |
| 2005/0043772 A1 * | 2/2005 | Stahmann et al. .............. 607/42 |

FOREIGN PATENT DOCUMENTS

| | | |
|---|---|---|
| EP | 1151718 | 11/2001 |
| EP | 1172125 | 1/2002 |
| EP | 1317943 | 6/2003 |
| WO | 99/04841 | 2/1999 |
| WO | WO0001438 | 1/2000 |
| WO | WO0017615 | 3/2000 |
| WO | 02/087696 | 7/2002 |
| WO | WO03075744 | 9/2003 |
| WO | WO2004062485 | 7/2004 |
| WO | WO2005028029 | 3/2005 |

OTHER PUBLICATIONS

Bradley et al., Sleep Apnea and Heart Failure, Park I: Obstructive Sleep Apnea, 107 Circulation 1671-1678 (2003).

Garrigue et al., Benefit of Atrial Pacing in Sleep Apnea Syndrome, 346 N. Engl. J. Med. 404-412 (2002). Abstract only.

Hilton et al., Evaluation of Frequency and Time-frequency Spectral Analysis of Heart Rate Variability as a Diagnostic Marker of the Sleep Apnea Syndrome, 37 Med. Biol. Eng. Comput. 760-769 (1999). Abstract only.

Javaheri et al., Sleep Apnea in 81 Ambulatory Male Patients with Stable Heart Failure: Types and Their Prevalences, Consequences, and Presentations, 97 Circulation 2154-2159 (1998).

Olusola et al., Nightcap: Laboratory and home-based evaluation of a portable sleep monitor, 32 Psychophysiology, 32-98 (1995). Abstract only.

Roche et al., Screening of Obstructive Sleep Apnea Syndrome by Heart Rate Variability Analysis, 100 Circulation 1411-1455 (1999).

Shahrokh, A Mechanism of Central Sleep Apnea In Patients With Heart Failure,341 N. Engl. J. Med. 949-954 (1999). Abstract only.

Vanninen et al., Cardiac Sympathovagal Balance During Sleep Apnea Episodes, 16 Clin. Physiol. 209-216 (1996). Abstract only.

Waldemark et al., Detection of Apnea using Short Window FFT Technique and Artificial Neural Network, 3390 SPIE International Society for Optical Engineering 122-133 (1998).

Young et al., The Occurrence of Sleep-Disordered Breathing Among Middle Aged Adults, N. Engl. J. Med. 1230-1235 (1993). Abstract only.

Dark et al., Breathing Pattern Abnormalities and Arterial Oxygen Desaturation During Sleep in the Congestive Heart Failure Syndrome, Chest, Jun. 1987, 6:833-6.

Hoffman et al., Cheyne-Stokes Respiration in Patients Recovering from Acute Cardiogenic Pulmonary Edema, Chest 1990, 97:410-12.

Rees et al., Paroxysmal Nocturnal Dyspnoea and Periodic Respiration, The Lancet, Dec. 22-29, 1979, pp. 1315-1317. Abstract Only.

Tkacova et al., Left Ventricular Volume in Patients with Heart Failure and Cheyne-Strokes Respiration during Sleep, Am. Journal, Respir. Crit. Care Med., vol. 156, pp. 1549-1555, 1997.

* cited by examiner

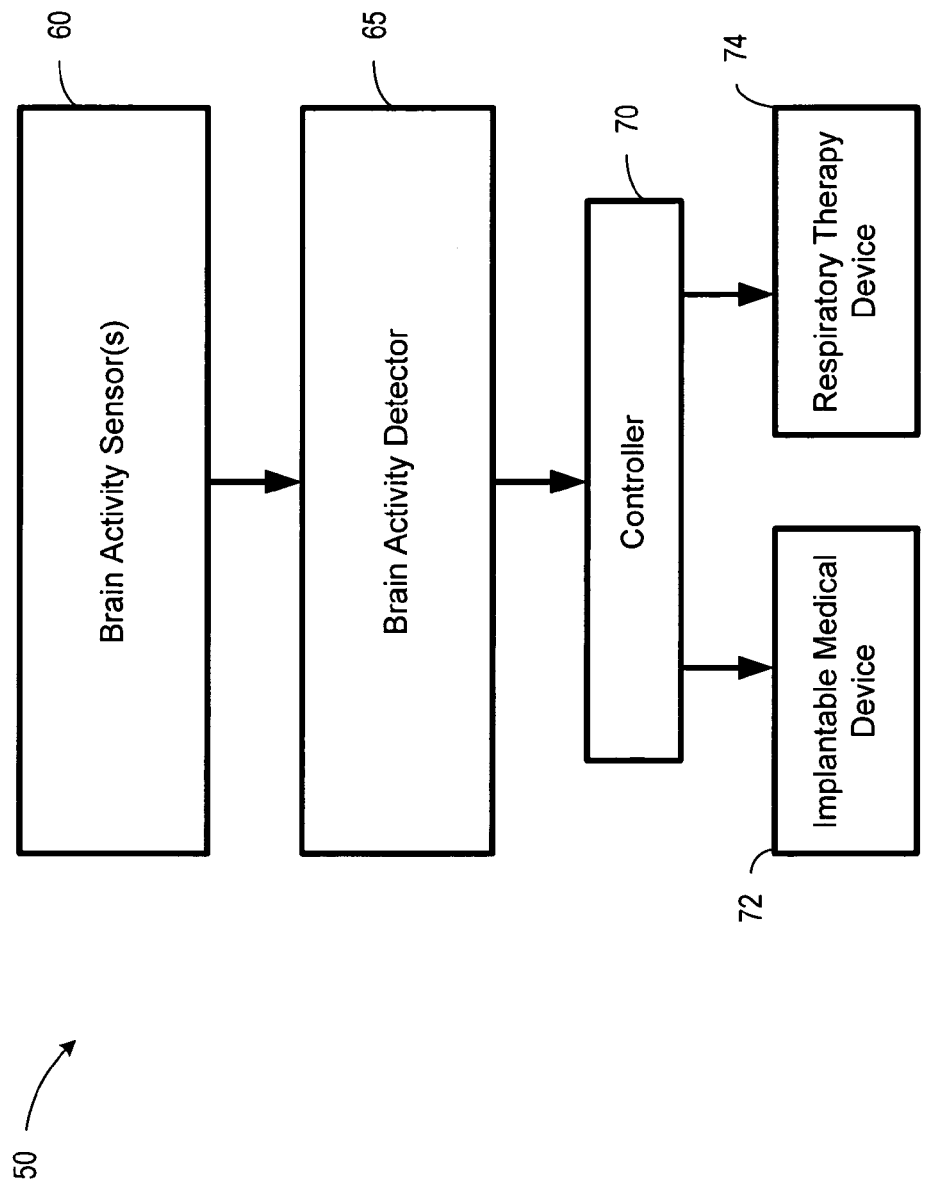

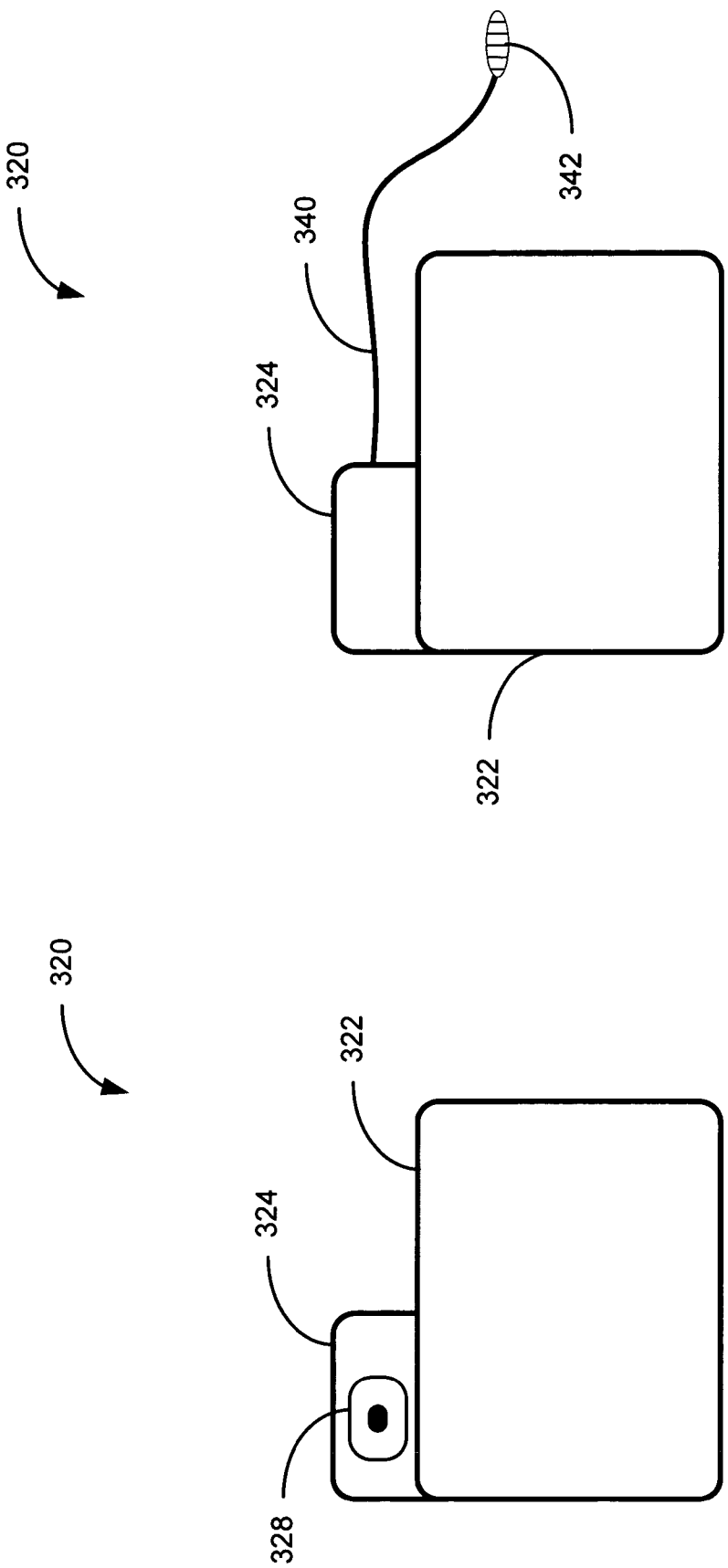

AUTOMATIC ACTIVATION OF MEDICAL PROCESSES

RELATED PATENT DOCUMENTS

This application claims the benefit of Provisional Patent Application Ser. No. 60/504,381, filed on Sep. 18, 2003, to which priority is claimed pursuant to 35 U.S.C. §119(e) and which is hereby incorporated herein by reference in its entirety.

FIELD OF THE INVENTION

The invention relates generally to implantable medical monitoring and/or stimulation systems and methods, and more particularly to monitoring and/or stimulation systems and methods that activate therapy based on brain activity.

BACKGROUND OF THE INVENTION

Disordered breathing refers to a wide spectrum of respiratory conditions that involve disruption of the normal respiratory cycle. Although disordered breathing typically occurs during sleep, the condition may also occur while the patient is awake. Unfortunately, disordered breathing is often undiagnosed. If left untreated, the effects of disordered breathing may result in serious health consequences for the patient.

Various types of disordered respiration have been identified, including, for example, apnea, hypopnea, dyspnea, hyperpnea, tachypnea, and periodic breathing, including Cheyne-Stokes respiration (CSR). Apnea is a fairly common disorder characterized by periods of interrupted breathing. Apnea is typically classified based on its etiology. One type of apnea, denoted obstructive apnea, occurs when the patient's airway is obstructed by the collapse of soft tissue in the rear of the throat. Central apnea is caused by a derangement of the central nervous system control of respiration. The patient ceases to breathe when control signals from the brain to the respiratory muscles are absent or interrupted. Mixed apnea is a combination of the central and obstructive apnea types. Regardless of the type of apnea, people experiencing an apnea event stop breathing for a period of time. The cessation of breathing may occur repeatedly during sleep, sometimes hundreds of times a night and sometimes for a minute or longer.

Periodic breathing is characterized by cyclic respiratory patterns that may exhibit rhythmic rises and falls in tidal volume. Cheyne-Stokes respiration is a specific form of periodic breathing wherein the tidal volume decreases to zero resulting in apneic intervals. The breathing interruptions of periodic breathing and CSR may be associated with central apnea, or may be obstructive in nature. CSR is frequently observed in patients with congestive heart failure (CHF) and is associated with an increased risk of accelerated CHF progression. Because of the cardiovascular implications, therapy for respiration-related sleep disorders is of particular interest.

Disordered breathing affects a significant percentage of people. Sleep disordered breathing is particularly prevalent and is associated with excessive daytime sleepiness, systemic hypertension, increased risk of stroke, angina and myocardial infarction. Respiratory disruption may be particularly serious for patients concurrently suffering from cardiovascular deficiencies, such as congestive heart failure.

SUMMARY OF THE INVENTION

Embodiments of the invention involve automatic control of therapies or other medical processes based on brain activity. Automatic control may involve automatic activation, de-activation and/or modification of such therapies and processes. In accordance with an embodiment of the invention, a system includes a sensor system having one or more sensors configured to sense signals related to the brain activity of the patient. A brain activity analyzer detects various brain states, including, for example, sleep state/stage and/or brain seizures. The brain activity detector may also be configured to discriminate between sleep and wakefulness. A controller uses the brain state detection information to control a medical system configured to perform at least one respiratory or cardiac process.

Other embodiments of the invention include at least one of an EEG sensor and an EMG sensor configured for one or more of detecting brain state. One or more sensors may be positioned on a respiratory mask of a respiratory device, such as a positive airway pressure therapy device. Further embodiments include a cardiac rhythm management device, wherein the cardiac process may involve one or both of a cardiac therapy process and a breathing therapy process. The cardiac process may further involve a diagnostic process and/or a monitoring process.

In accordance with another embodiment of the invention, a method involves sensing signals related to brain state and determining the brain state of a patient based on the sensed signals. At least one respiratory or cardiac medical process is activated, de-activated, modified or otherwise controlled based on the patient's brain state.

Further embodiments of methods in accordance with the invention involve sensing the signals related to brain state using EEG signals and/or EMG signals. Sensing signals related to brain state may further involve sensing signals related to sleep stage. Sensing signals related to brain state may involve sensing seizure, and activating the medical process may involve activating, de-activating, modifying or otherwise controlling arrhythmia therapy based on seizure detection.

BRIEF DESCRIPTION OF THE DRAWINGS

FIG. 1A is a flow chart illustrating a method of controlling a medical process using brain state information in accordance with embodiments of the invention;

FIGS. 1F-1H and 1J are diagrams illustrating various configurations of sensors coupled to an implanted medical device that uses brain state information to activate, de-activate, and/or modify therapy in accordance with embodiments of the invention;

Figure 1B:
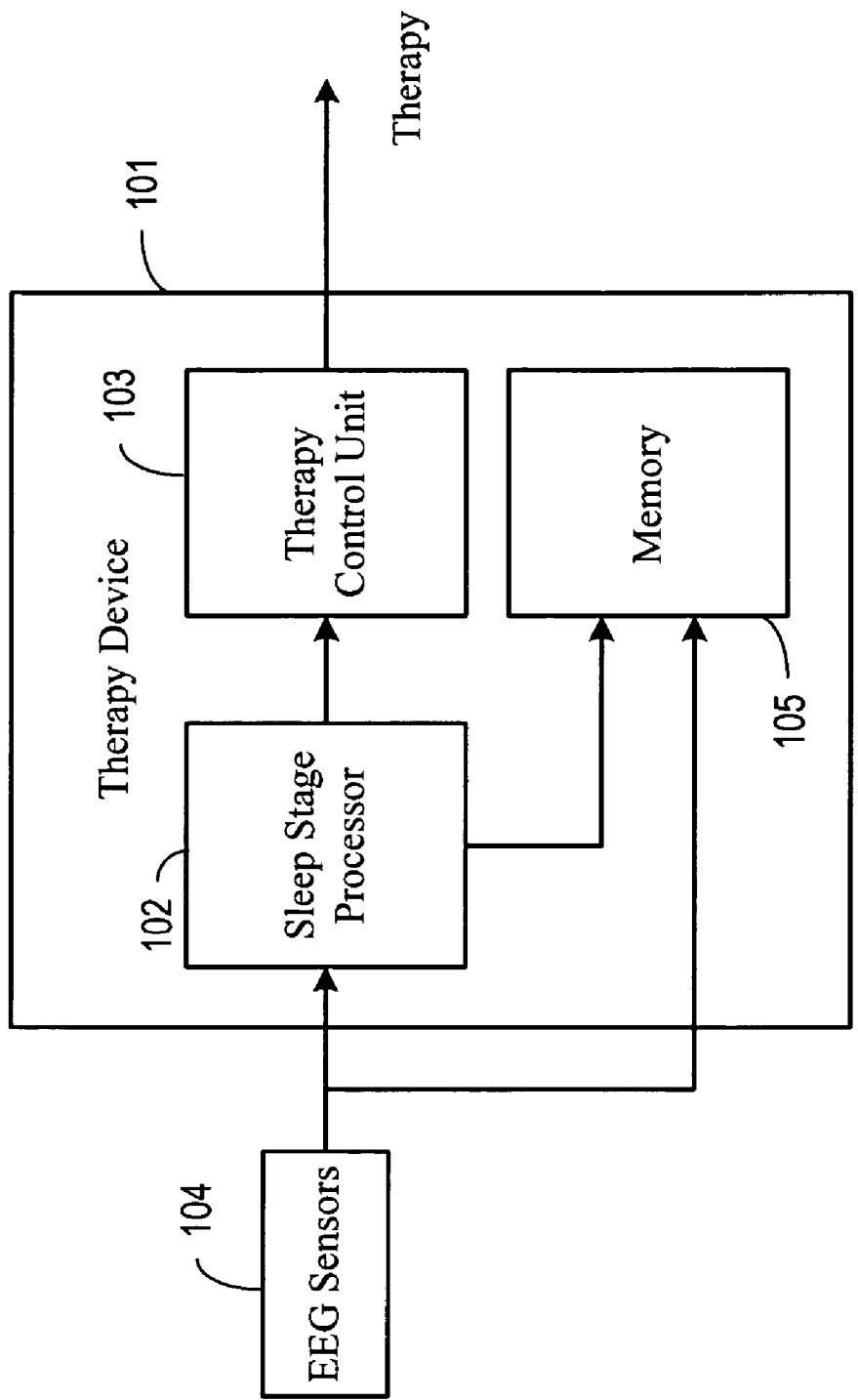
FIGS. 1B-1D are block diagrams of systems implementing control of medical processes using brain activity information in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which are shown by way of illustration, various embodiments by which the invention may be practiced. It is to be understood that other embodiments may be utilized, and structural and functional changes may be made without departing from the scope of the invention.

Detection of brain state may be used to trigger sleep-time therapy in a respiratory and/or cardiac device. A patient's brain state may be determined by sensing brain activity of the patient, which may provide normal brain state information such as sleep state/stage, as well as abnormal brain state information such as seizure information. It may also be useful to trigger patient monitoring and/or data collection for diagnostic purposes during sleep. Data acquired during sleep may assist in diagnosing various sleep-related disorders. The collected data may be stored, displayed, printed, or transmitted to a separate device.

Embodiments of the invention include automatic activation, de-activation and/or modification of therapy based on sleep stage. Alternatively, or additionally, sleep stage information may be used to automatically activate, de-activate and/or modify a number of processes, including for example, patient monitoring processes and/or diagnostic processes. Therapies may be selectively activated, de-activated, and/or modified based on sleep stage. For example, during deeper sleep stages, less invasive therapies such as a pacing therapy may be more desirable than a CPAP therapy. Embodiments may further provide for discrimination between sleep and wakefulness.

A number of disorders, for example, sleep disordered breathing and movement disorders such as Periodic Limb Movement Disorder (PLMD), occur primarily while the patient is asleep. It may be useful to provide a first therapy while the patient is awake and to trigger a second therapy while the patient is asleep using brain state information.

Other embodiments of the invention include a device that detects brain state, such as by using EEG sensor information, and based on the detected brain state, initiates, de-activates or alters therapy provided by a CRM device and/or a respiratory device. This allows closed loop control of sleep-disordered breathing based on sleep stage, which may be determined from the EEG sensor information. The EEG sensor information may also be used to detect seizures, and based on seizure detection, control CRM therapy to treat potential arrhythmias.

A significant percentage of patients between the ages of 30 and 60 years experience some symptoms of disordered breathing. Although disordered breathing may occur while the patient is awake, it more often occurs during sleep. Sleep disordered breathing is associated with excessive daytime sleepiness, systemic hypertension, increased risk of stroke, angina and myocardial infarction. Disordered breathing is particularly prevalent among congestive heart failure patients, and may contribute to the progression of heart failure.

Various therapies have been used to treat central and/or obstructive disordered breathing episodes. Obstructive sleep apnea has been associated with prolapse of the tongue and its surrounding structure into the pharynx, thus occluding the respiratory pathway. A commonly prescribed treatment for obstructive apnea is continuous positive airway pressure (CPAP). A CPAP device delivers air pressure through a nasal mask worn by the patient. The application of continuous positive airway pressure keeps the patient's throat open, reducing or eliminating the obstruction causing apnea. The term xPAP will be used herein as a generic term for any method, system, or device useful for treatment of apnea, including devices using forms of positive airway pressure, whether continuous pressure or variable pressure, as well as gas therapy and/or oxygen therapy devices.

Cardiac stimulation may alternately or additionally be used as a therapy for disordered breathing. Therapy methods for disordered breathing based on cardiac electrical stimulation are described in commonly owned U.S. Publication Nos. 2005/0039745 and 2005/0043772, both of which are incorporated by reference herein.

Disorders and diseases affecting the interdependent physiological systems of the human body may be more effectively diagnosed and treated using a coordinated approach. Various embodiments of the invention are implemented using medical systems employing one or a number of patient-external and/or patient-internal medical systems. Medical systems may communicate or otherwise operate in concert or in a stand-alone manner to provide more comprehensive patient monitoring, diagnosis, and therapy.

The following discussion, with reference to FIGS. 1A-1H and 1J, describes embodiments of the invention involving automatic activation, de-activation, modification and/or control of therapy based on sleep stage. Sleep staging may be detected using various approaches, including, for example, by detecting brain activity, skeletal muscle movement, heart rate or other cardiac timing or intervals (e.g., PR interval), respiratory patterns, and/or other activity/signal that can be used as a surrogate measurement of sleep. The processes and systems exemplified by these embodiments may be implemented alone or in combination with one or more processes and systems exemplified by other embodiments described herein to provide a coordinated approach to patient monitoring, diagnosis, and/or therapy.

Although disordered breathing may occur while the patient is awake, the disorder is much more prevalent while the patient is sleeping. In various embodiments of the invention, sleep stage information is used to enhance sleep disordered breathing therapy and/or diagnosis of a variety of sleep related disorders.

In accordance with one embodiment, sleep stage detection may be used to trigger therapy for disordered breathing. Using this approach, administration of disordered breathing therapy may be coordinated with a particular sleep stage. For example, disordered breathing episodes are typically more frequent during stage 1 or stage 2 sleep. The system may use sleep stage detection to deliver the therapy during these sleep stages. REM sleep and sleep stages 3 and 4 are the most restful sleep stages, therefore it is desirable to avoid interruption of sleep during these stages. The system may terminate or reduce the level of therapy during REM sleep and sleep stages 3 and 4 when avoidance of sleep interruptions are most desirable.

Sleep stage detection may be accomplished using a number of techniques, including, for example, a technique using muscle atonia sensors described in commonly owned U.S. Publication No. 2005/0043652, which is hereby incorporated herein by reference. Sleep stage detection may also be effected using patient-internal or patient-external sensors, including, for example EEG sensors and/or EMG sensors. In one configuration, the sensors, e.g., EEG and/or EMG sensors, used in combination with a respiratory therapy device, such as an xPAP device, may be positioned on the xPAP mask. Sleep stage detection may also be derived from heart rate, cardiac PR intervals (or other cardiac timing), tidal volume, respiratory rate, minute ventilation, body core temperature, or other physiological measurements that are affected by autonomic control.

Sleep stage information may also be valuable in the context of diagnosing various disorders, including sleep-related disorders. In accordance with one embodiment, sleep information, including sleep onset, offset, sleep stages, sleep efficiency, sleep latency, and the number and degree of arousals may be collected by the system for storage, display, or transmission to a remote device. The sleep-related information may be evaluated along with information about detected disordered breathing episodes to more fully understand how sleep disordered breathing affects a particular patient. The use of EEG sensors also allows detection of abnormal brain activity, including seizures. The EEG sensor information may be collected and used for a variety of diagnostic and therapeutic purposes.

FIG. 1A is a flow chart illustrating a system 50 useful for activating, de-activating or modifying a medical process using brain state information in accordance with embodiments of the invention. The system 50 involves sensing brain activity with a sensor 60, either directly, such as by using an EEG sensor to measure brain-waves, or indirectly, such as by using an EMG sensor to measure muscular response to neurostimulation. A brain activity detector 65 receives information from the sensor 60 and determines a brain state, which is used by a controller 70. The controller 70 may control one or both of an implantable medical device 72 and a respiratory therapy unit 74. The implantable medical device 72 and/or the respiratory therapy unit 74 provides therapy based on information about the sensed brain activity.

A system utilizing sleep stage sensors in connection with the control of diagnostic and/or therapeutic functions of a disordered breathing system in accordance with an embodiment of the invention is illustrated in FIG. 1B. In this embodiment, patient-internal or patient-external sensors 104, for example EEG and/or EMG sensors, are coupled to a therapy device 101. The therapy device 101 includes a sleep stage processor 102 that analyzes the sensor signals to detect the patient's sleep state, including sleep offset, onset, and stages of sleep.

The sleep stage processor 102 is coupled to a therapy control unit 103. The therapy control unit 103 may control various types of therapy, including, for example, disordered breathing therapy, cardiac pacing therapy, respiratory therapy, electrical stimulation therapy, muscle stimulation therapy, nerve stimulation therapy, and/or pharmacological therapy, among other therapy types. The therapy control unit 103 uses the sleep information to initiate, terminate or adjust therapy to the patient based on the patient's sleep stage.

The therapy device 101 may further include a memory 104 that receives and stores information from the sleep stage processor 102, the sensors 104 and/or other components. The information stored in the memory 105 may be displayed and/or downloaded to a remote device, or used for a variety of diagnostic purposes.

Figure 1C:
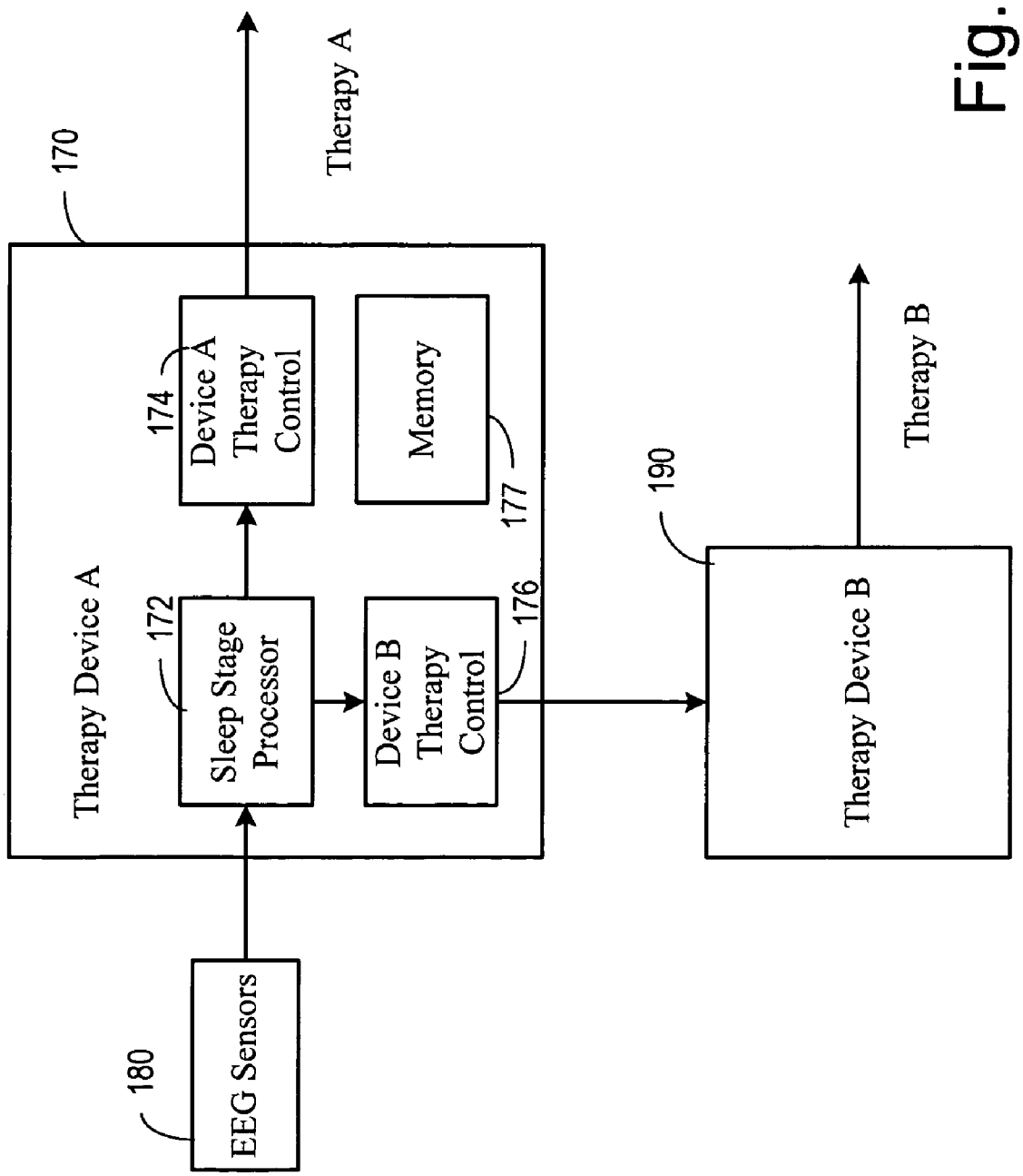

Another embodiment of the invention is illustrated in FIG. 1C. In accordance with this embodiment, a first therapy device 170 is used to control therapy delivery of a second therapy device 190. The first therapy device 170 includes a sleep stage processor 172 coupled to sensors 180, e.g., EEG and/or EMG sensors. The sleep stage processor receives signals from the sensors 180 and analyzes the sensor signals to determine sleep onset, offset, and stages of sleep.

Sleep stage information is transferred from the sleep stage processor 172 to a first therapy control unit 174 and a second therapy control unit 176. The therapy control units 174, 176 use the sleep stage information to initiate, terminate or modify the therapy delivered by the first and the second therapy devices 170, 190, respectively, based on the patient's sleep state.

The first therapy device 170 may also include a memory 177 that receives and stores information from the sleep stage processor 172, the sensors 180 and/or other components. The information stored in the memory 177 may be displayed and/or downloaded to a remote device, or used for a variety of diagnostic purposes.

Figure 1D:
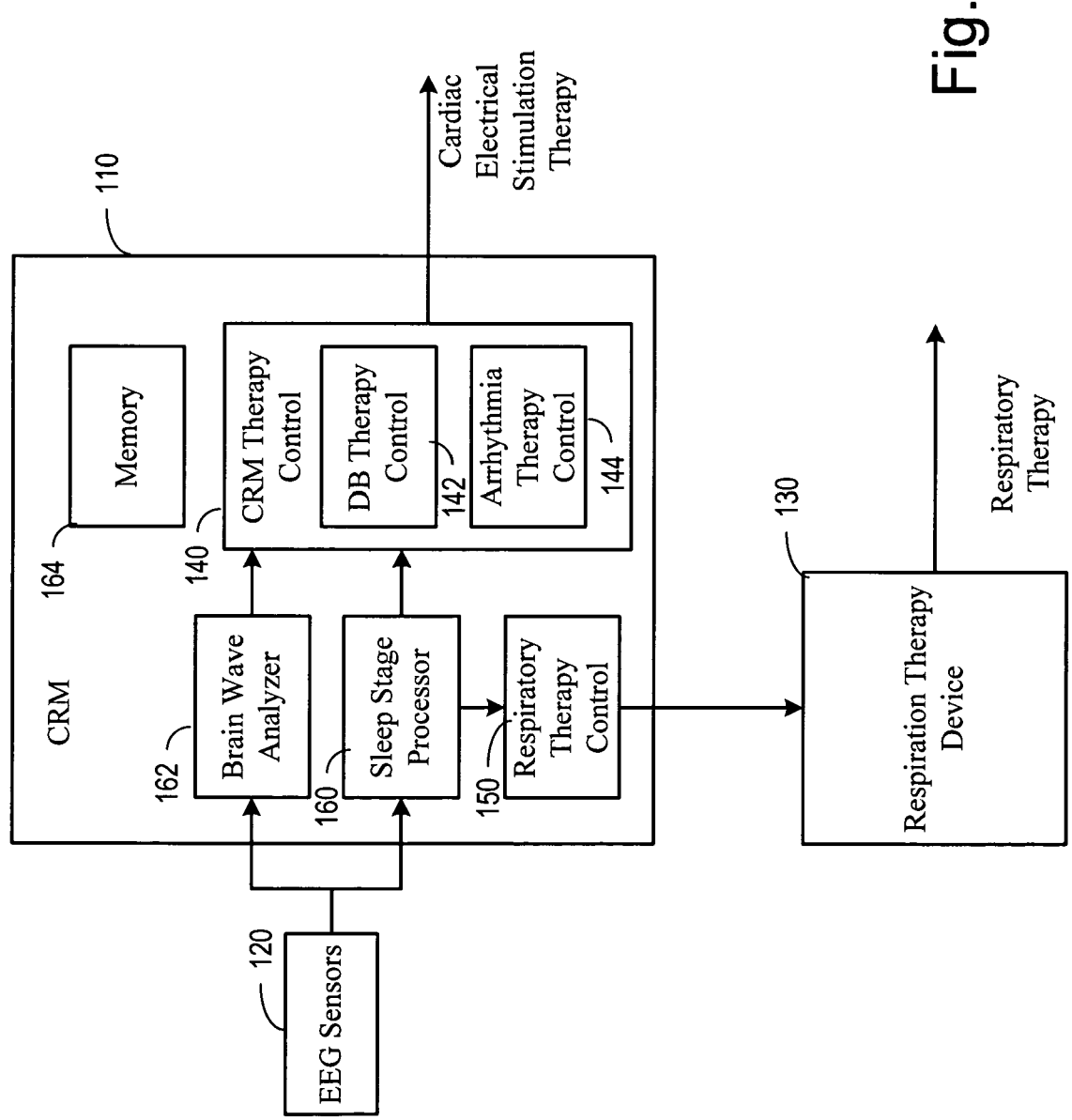

A further embodiment of the invention is illustrated in FIG. 1D. According to this embodiment, first and second therapy devices 110, 130 deliver first and second therapies to a patient. The first therapy device 110 may be implemented as a CRM device, providing cardiac pacing and/or defibrillation therapies to treat various arrhythmias and/or to provide resynchronization therapy, for example. The CRM device 110 may also deliver electrical stimulation therapy to the heart to treat disordered breathing.

The second therapy device 130 may be implemented as respiratory therapy device, such as an xPAP device. The xPAP device 130 delivers air or other gas therapy at a controlled pressure to the patient's airway.

EEG sensors 120 are coupled to a sleep stage processor 160 located in the CRM device 110. Other sensors, such as EMG sensors, may also be included. Signals from the EEG and/or other sensors 120 are analyzed by the sleep stage processor 160 to determine various stages of sleep, including sleep onset, offset, sleep stage, the number and frequency of arousals, and the degree of arousal.

Information from the sleep stage processor 160 is provided to the respiratory therapy controller 150 located in the CRM device 110. The respiratory therapy controller 150 uses the sleep stage information to initiate, terminate, or modify the respiratory therapy based on the sleep stage.

Information from the sleep stage processor 160 and a brain wave analyzer 162 is provided to the CRM therapy controller 140. The CRM therapy controller 140 includes a disordered breathing (DB) therapy control unit 142 that uses the sleep stage information to initiate, terminate, or modify electrical stimulation DB therapy delivered by the CRM device 110 based on the patient's sleep state.

The CRM therapy controller 140 may further include an arrhythmia therapy control unit 144. Information from the sleep stage processor 160 and the brain wave analyzer 162 may be used by the arrhythmia therapy control unit to 144 initiate, terminate, or modify arrhythmia therapy delivered to the patient.

For example, the CRM therapy controller 140 may decrease the cardiac pacing rate to a sleep rate upon sleep onset and raise the pacing rate at sleep offset. Further, the CRM therapy controller 140 may adjust the pacing therapy delivered to the patient during proarrhythmic sleep periods, such as REM sleep or the during morning arousal. In one example, the arrhythmia therapy control unit 144 may deliver atrial overdrive pacing during proarrhythmic sleep periods to prevent the occurrence of arrhythmia.

The EEG sensor signals may also be used by a brain wave analyzer 162 to evaluate brain activity. The brain wave analyzer 162 detects abnormal brain activity, such as seizures. Patients may have seizures during the night and not realize that the seizures have occurred. Some seizures are accompanied by cardiac rhythm disturbances. The brain wave analyzer 162 may detect the occurrence of seizures and provide information about the seizures to the arrhythmia therapy control unit 144. The arrhythmia therapy control unit 144 may modify the CRM therapy to treat cardiac rhythm disturbances cause by, or associated with, seizures. The arrhythmia therapy control unit 144 may also withhold therapy for rhythm disturbances that are associated with seizures.

The CRM device 110 may include a memory 164 for storing information from the sleep stage processor 160, the brain wave analyzer 162 and other components of the CRM device 110. Stored information may be transferred to a display or other device.

Figure 1E:
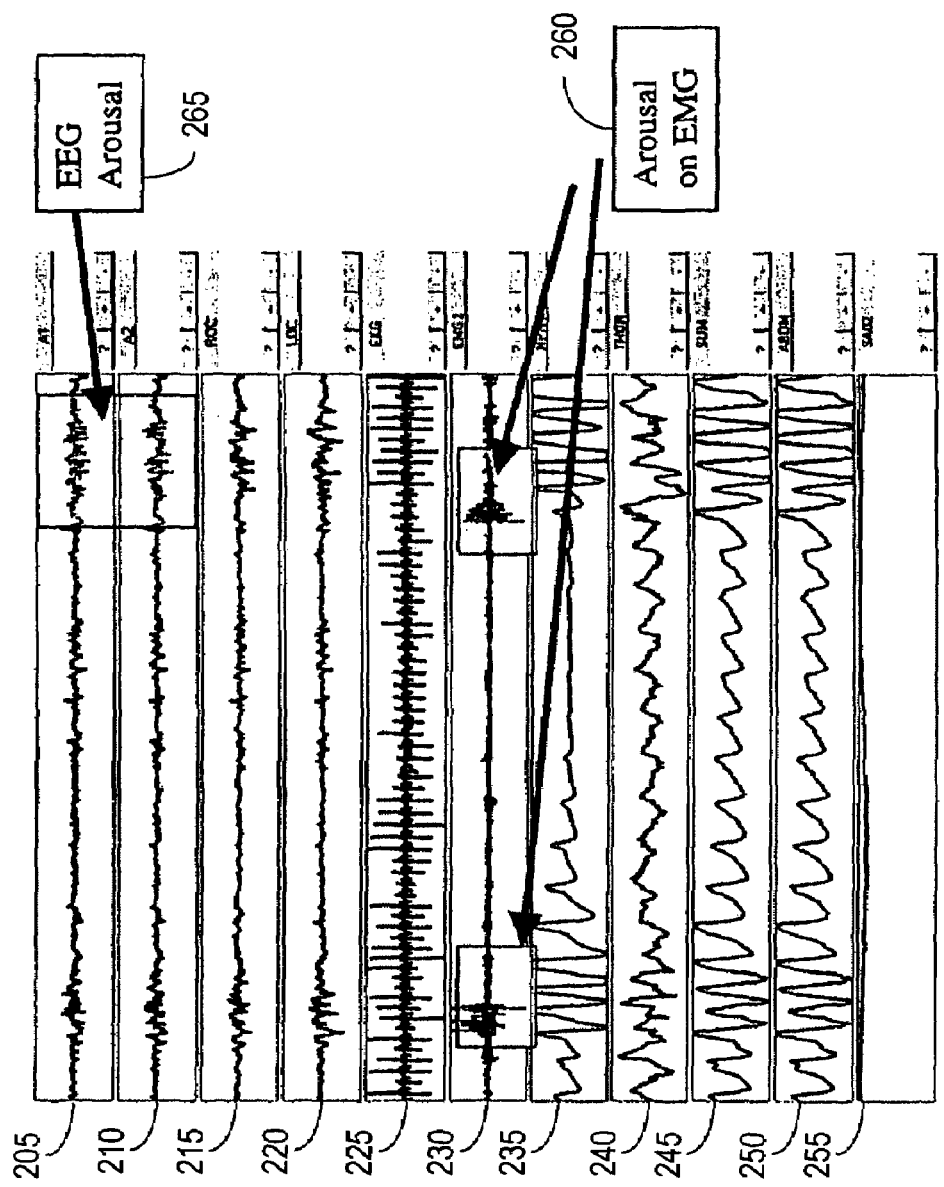
FIG. 1E illustrates graphs of signals from an EEG sensor and an EMG sensor useful for determining brain state in accordance with embodiments of the invention.
Figure 1G:
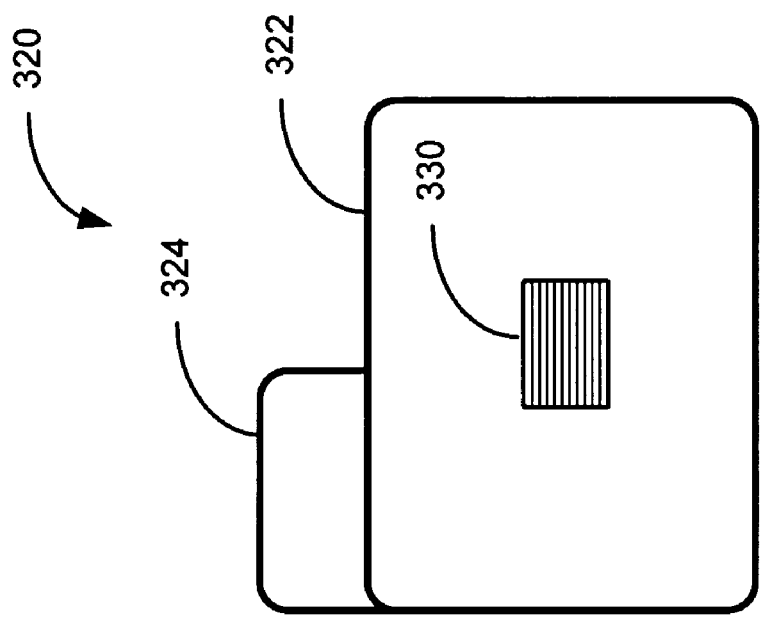
Figure 1F:
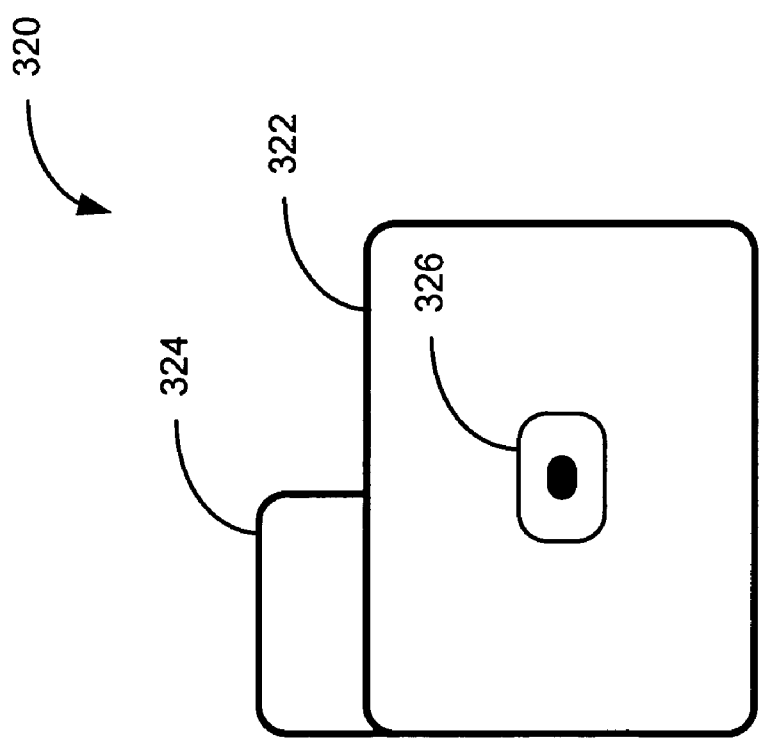

Autonomic arousal responses, as detected using EEG sensors and EMG sensors, are indicative of brain state. Referring now to FIG. 1E, a sleep study sensor array output is illustrated including an apnea event terminating in an arousal. Arousal may be detected from changes in the sympathetic or parasympathetic nervous system. These changes may be either short-term (i.e., changes associated with individual arousals) or long-term (i.e., aggregate effect of multiple arousals). A short-term effect of arousal includes, for example, the activation of sympathetic nerve activities. Sympathetic or parasympathetic changes, or the changes of autonomic balance, may be assessed, for example, by heart rate variability (HRV), which may be readily detected using a CRM device.

Arousal information may be also used by the sleep stage processor 160 to augment disordered breathing detection. For example, arousal information may be used to confirm occurrences of disordered breathing. Arousal information may be used to distinguish between correctly and incorrectly identified disordered breathing occurrences indicated by the disordered breathing detector. Further, information from arousal detection may be used to separate disordered breathing episodes, e.g., apnea and/or hypopnea, followed by arousal versus those terminated without arousal. The disordered breathing events that are followed by arousal are considered to be the most disruptive, as these arousals interrupt the normal course of sleep and prevent the patient from receiving a full sleep cycle each night. Detecting these types of disordered breathing events may enhance the specificity of disordered breathing detection. Further description of the use of arousal information in combination with cardiac and xPAP therapies is described in commonly-owned, U.S. Publication No. 2005/0076908 and hereby incorporated herein by reference.

In the graphs of FIG. 1E, the abscissa of all the graphs is the same time period during the sleep analysis of a patient. The ordinate of each of the graphs is the signal amplitude of the respective sensor. Traces 205, 210, 215, and 220 are the top, second, third, and fourth traces respectively, plotted from electrodes adapted to produce electroencephalograms (EEG). Evident in all four traces, but particularly pointed out in traces 205 and 210 is an EEG detected arousal 265. A trace 225 provides an electrocardiogram (EKG) of the heartbeats during the time period of the graph. A trace 230 provides an electromyogram defining muscular movement during the time period of the graph. Particularly evident in the trace 230 are arousals indicated by an arousal on EMG 260.

Traces 235, 240, 245, and 250 depict pulmonary activity as sensed by bands placed around the torso. For example, trace 240 is produced using a band encircling the thorax of the patient, and trace 250 is produced using a band encircling the abdomen of the patient. Pulmonary activity may also be sensed through the use of internal sensors, such as, for example, thoracic impedance sensors and minute ventilation sensors as will be described further below. Trace 255 depicts the blood oxygen saturation level of the patient.

FIGS. 1F-1H and 1J illustrate various configurations of an EMG sensor mechanically coupled to an implanted medical device 320, such as an implantable pacemaker or implantable cardioverter/defibrillator in accordance with embodiments of the invention, which may be useful for indirectly detecting brain state and activating, de-activating or modifying medical processes, such as by detecting arousal, sleep-state, seizure, or other indirect detection of brain state and/or brain activity. The implantable medical device 320 may include a housing 322 enclosing the medical device circuitry and a header 324 for coupling a lead system 340 to the circuitry of the medical device 320.

An EMG sensor may be implemented, for example, using an electromyogram (EMG) electrode 326 or force responsive sensor 330 positioned on the housing 322 of the medical device 320 as illustrated in FIGS. 1H and 1J, respectively. FIG. 1H illustrates an EMG sensor 328 positioned on the header 324 of the medical device 320. Alternatively, an EMG sensor 342, e.g., EMG electrode or strain gauge, may be positioned on the lead system 340 or may be coupled to the housing 322 through a catheter or lead system 340, such as by using the header 324, as illustrated in FIG. 1J.

Figure 2:
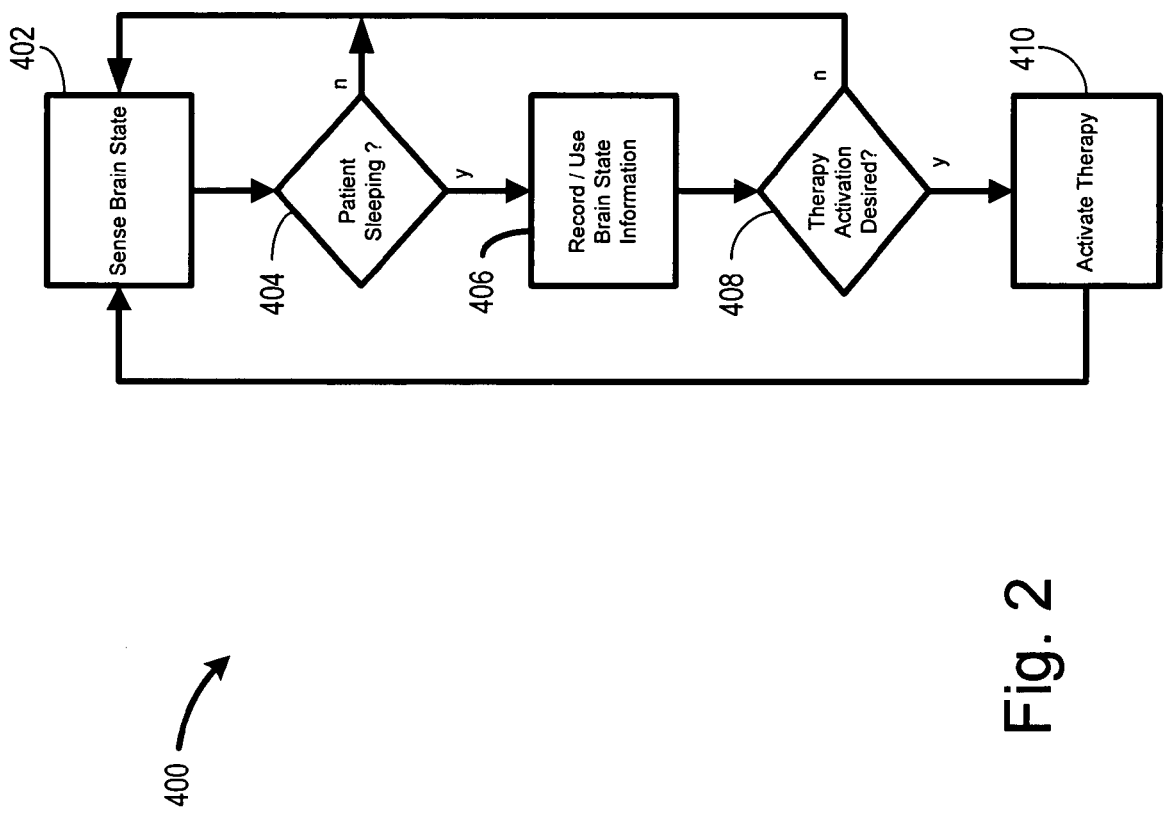
FIG. 2 is a flow chart illustrating a brain state algorithm based on signals from an EEG sensor in accordance with embodiments of the invention.

FIG. 2 illustrates a method 400 for implantably sensing and detecting brain state. A brain state sense signal is sensed at a block 402. Brain state may be sensed, for example, directly using EEG sensors, and/or indirectly using ECG sensors, EEG sensors, EMG sensors, transthoracic impedance sensors, or other sensors suitable for determining patient brain state. If the patient is sleeping, brain state may be detected using the brain state sense signal illustrated by determination block 404.

The brain state detected at determination block 404 provides various types of information recorded at block 406. For example, date, time, sensor data, sense signal amplitudes and/or cycle lengths. This and other information may be useful for updating, developing, and/or determining an arousal index, an apnea/hypopnea index, a composite index and other parameters useful for patient diagnosis and treatment, such as the automatic activation, de-activation or modification of medical processes. This information may be useful for detecting abnormal brain activity, such as seizures. The information recorded at block 406 may be useful, for example, to predict, verify, classify, and/or determine the severity of a disordered breathing episode and abnormal brain activity.

If intervention and/or treatment is desired at determination block 408, the intervention and/or treatment may be performed at block 410 before re-starting the method 400. For example, the intervention at block 410 may be the automatic activation of a medical process, modification of a patient's CRM stimulation, modification of a disordered breathing therapy, or other desirable action.

Figure 3:
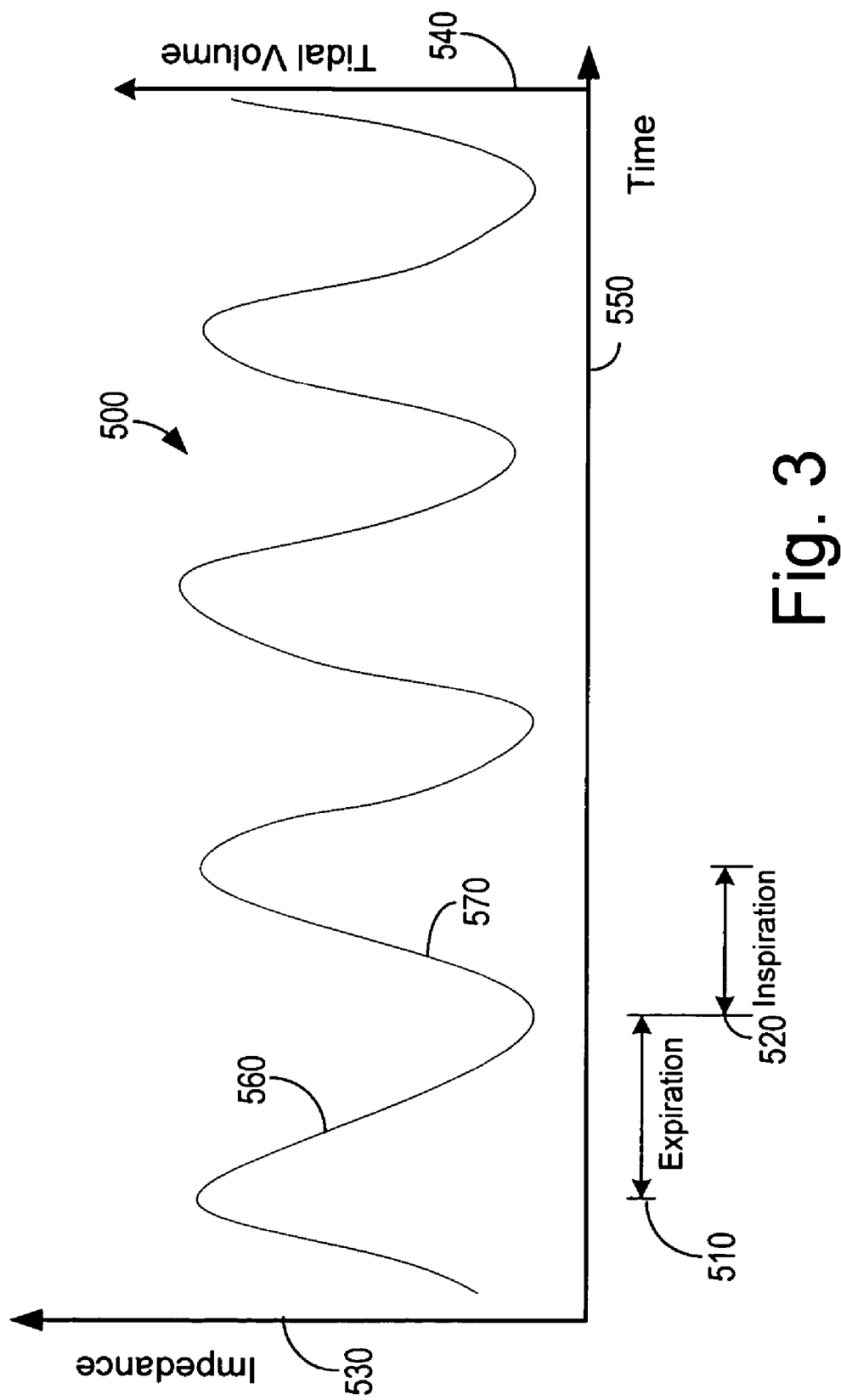
FIG. 3 is a graph of a normal respiration signal measured by a transthoracic impedance sensor that may be utilized for monitoring, diagnosis and/or therapy in accordance with embodiments of the invention.

Referring now to FIG. 3, an impedance signal 500 is illustrated. Transthoracic impedance may be useful for detecting sleep-state and other indirect measurements of brain activity, such as seizures, as well as breathing disorders. The impedance signal 500 may be developed, for example, from an impedance sense electrode in combination with a CRM device. The impedance signal 500 is proportional to the transthoracic impedance, illustrated as an Impedance 530 on the abscissa of the left side of the graph in FIG. 3.

The impedance 530 increases during any respiratory inspiration 520 and decreases during any respiratory expiration 510. The impedance signal 500 is also proportional to the amount of air inhaled, denoted by a tidal volume 540, illustrated on the abscissa of the right side of the graph in FIG. 3. The variations in impedance during respiration, identifiable as the peak-to-peak variation of the impedance signal 500, may be used to determine the respiration tidal volume 540. Tidal volume 540 corresponds to the volume of air moved in a breath, one cycle of expiration 510 and inspiration 520. A minute ventilation may also be determined, corresponding to the amount of air moved per a minute of time 550 illustrated on the ordinate of the graph in FIG. 3.

The onset of breathing disorders may be determined using the impedance signal 530, and detected breathing disorder information may be used to activate or modify therapy in accordance with the present invention. During non-REM sleep, a normal respiration pattern includes regular, rhythmic inspiration-expiration cycles without substantial interruptions. When the tidal volume of the patient's respiration, as indicated by the transthoracic impedance signal, falls below a hypopnea threshold, then a hypopnea event is declared. For example, a hypopnea event may be declared if the patient's tidal volume falls below about 50% of a recent average tidal volume or other baseline tidal volume value. If the patient's tidal volume falls further to an apnea threshold, e.g., about 10% of the recent average tidal volume or other baseline value, an apnea event is declared.

An adequate quality and quantity of sleep is required to maintain physiological homeostasis. Prolonged sleep deprivation or periods of highly fragmented sleep ultimately has serious health consequences. Chronic lack of sleep may be associated with various cardiac or respiratory disorders affecting a patient's health and quality of life. Methods and systems for collecting and assessing sleep quality data are described in commonly owned U.S. Publication No. 2005/0042589, and incorporated herein by reference in its entirety.

Evaluation of the patient's sleep patterns and sleep quality may be an important aspect of providing coordinated therapy to the patient, including respiratory and cardiac therapy.

Figure 4:
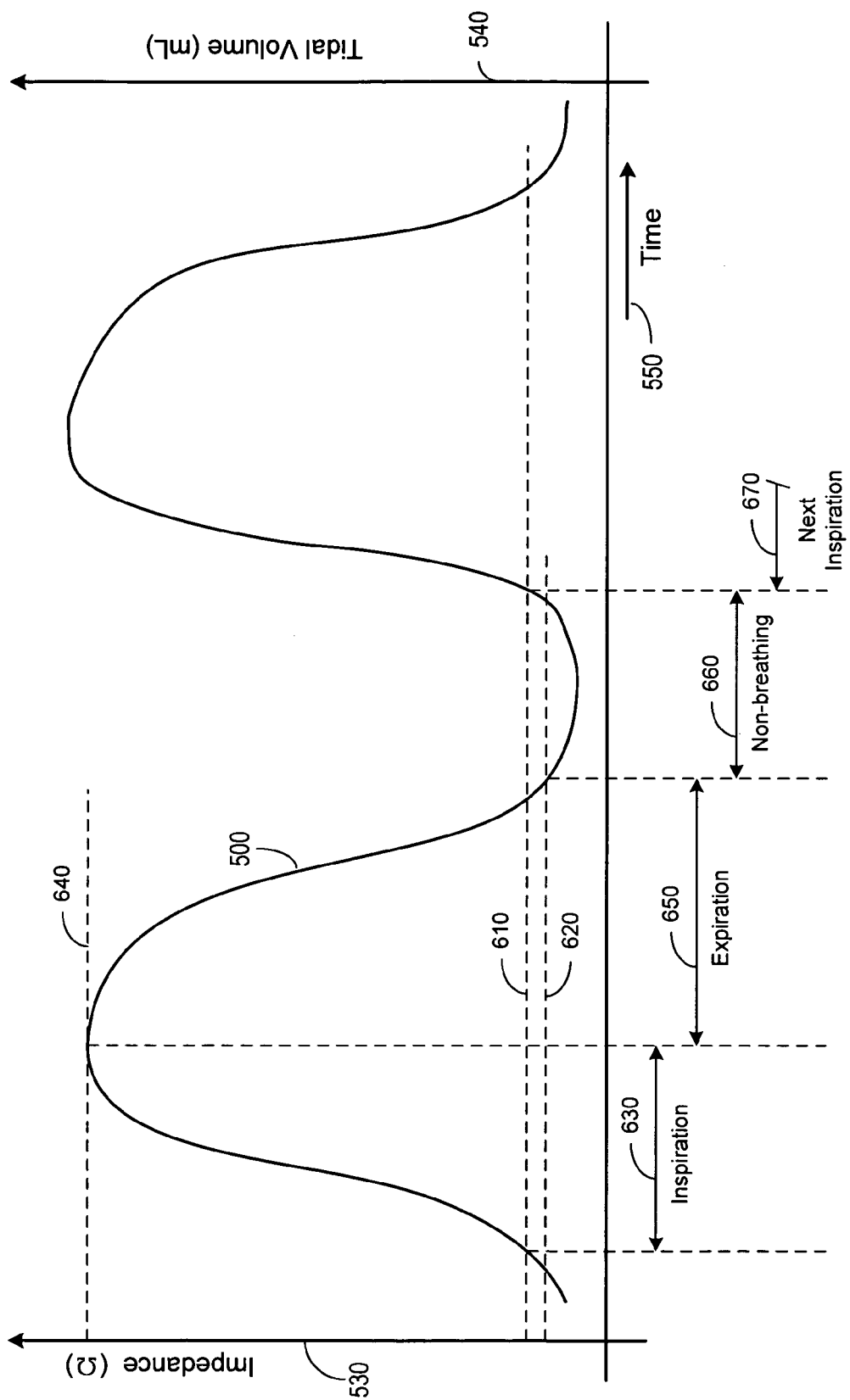
FIG. 4 is a respiration signal graph illustrating respiration intervals used for disordered breathing detection according to embodiments of the invention.
Figure 5:
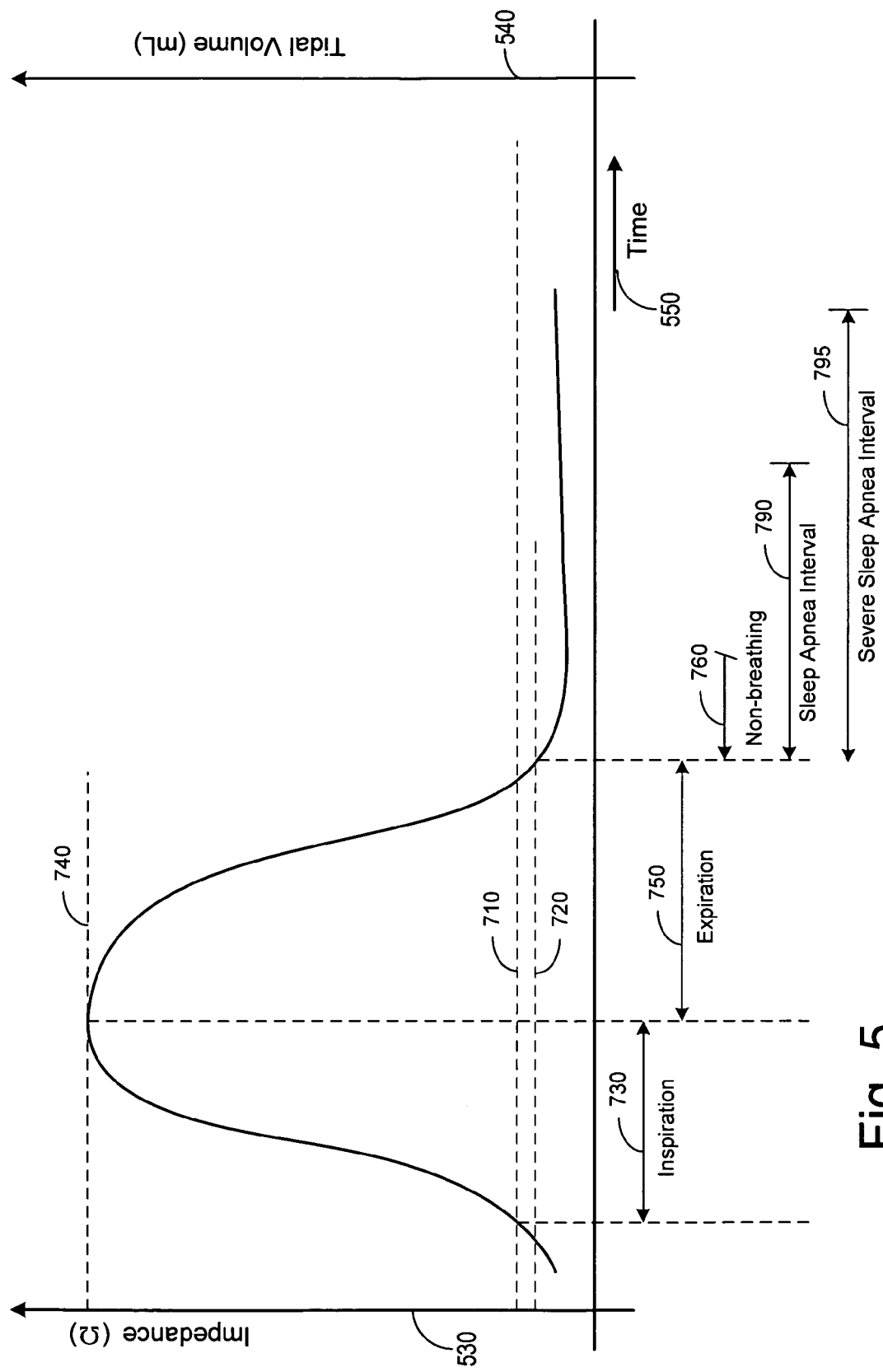
FIG. 5 is a graph of a respiration signal illustrating various intervals that may be used for detection of apnea in accordance with embodiments of the invention.
Figure 6:
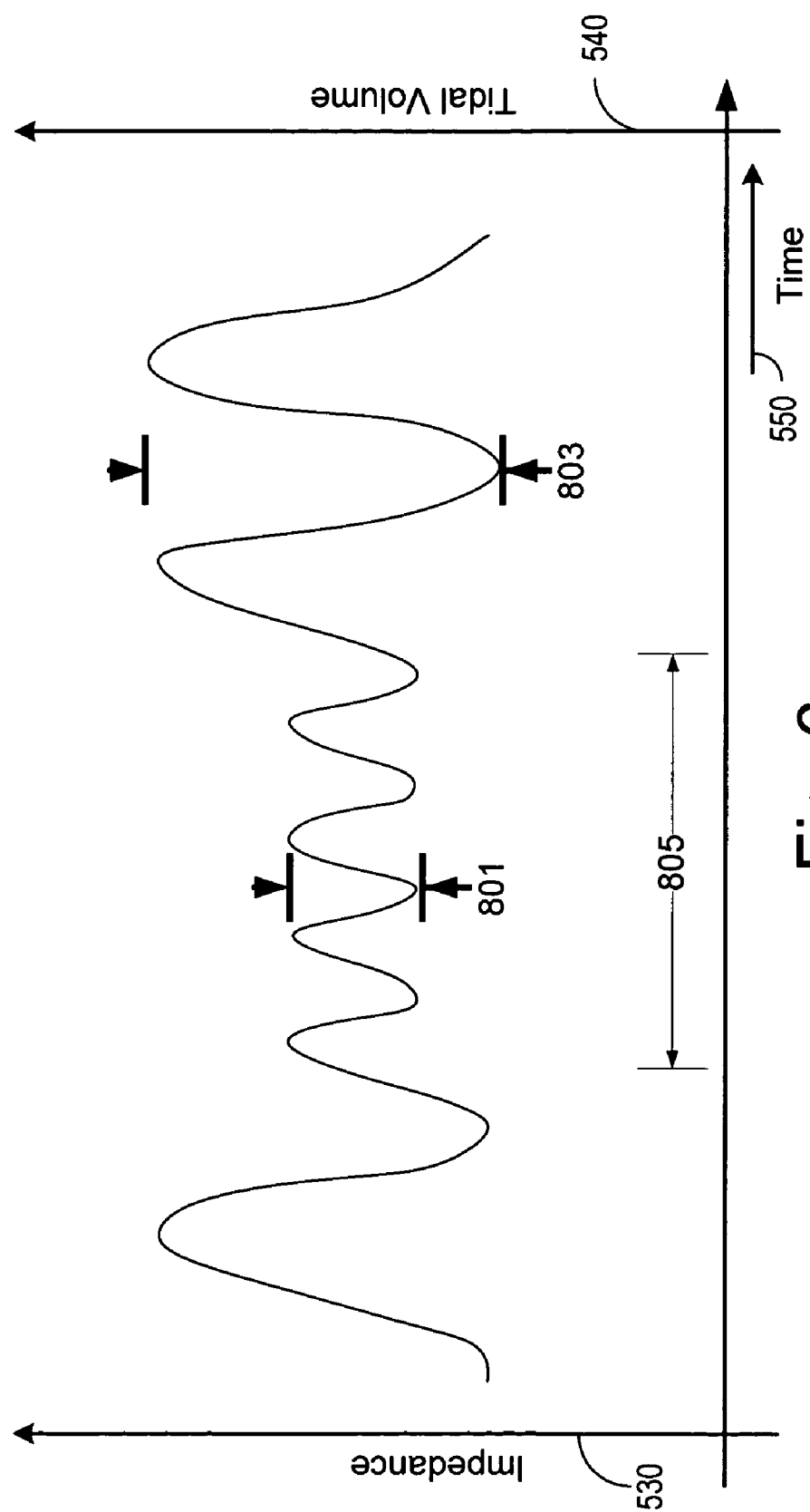
FIG. 6 is a respiration graph illustrating abnormally shallow respiration utilized in detection of disordered breathing in accordance with embodiments of the invention.

FIGS. 4-6 are graphs of transthoracic impedance and tidal volume, similar to FIG. 3 previously described. As stated earlier, using transthoracic impedance is one indirect method of determining brain state, such as by detecting sleep state, arousal, and disordered breathing, for example. As in FIG. 3, FIGS. 4-6 illustrate the impedance signal 500 proportional to the transthoracic impedance, again illustrated as Impedance 530 on the abscissa of the left side of the graphs in FIGS. 4-6. The impedance 530 increases during any respiratory inspiration 520 and decreases during any respiratory expiration 510. As before, the impedance signal 500 is also proportional to the amount of air inhaled, denoted the tidal volume 540, illustrated on the abscissa of the right side of the graph in FIGS. 4-6. The magnitude of variations in impedance and tidal volume during respiration are identifiable as the peak-to-peak variation of the impedance signal 500.

FIG. 4 illustrates respiration intervals used for disordered breathing detection useful in accordance with embodiments of the invention. Respiration intervals are used to detect apnea and hypopnea, as well as provide other sleep-state information for activating, de-activating or modifying therapy in accordance with the present invention. Detection of disordered breathing may involve defining and examining a number of respiratory cycle intervals. A respiration cycle is divided into an inspiration period corresponding to the patient inhaling, an expiration period, corresponding to the patient exhaling, and a non-breathing period occurring between inhaling and exhaling. Respiration intervals are established using an inspiration threshold 610 and an expiration threshold 620. The inspiration threshold 610 marks the beginning of an inspiration period 630 and is determined by the transthoracic impedance signal 500 rising above the inspiration threshold 610. The inspiration period 630 ends when the transthoracic impedance signal 500 is a maximum 640. The maximum transthoracic impedance signal 640 corresponds to both the end of the inspiration interval 630 and the beginning of an expiration interval 650. The expiration interval 650 continues until the transthoracic impedance 500 falls below an expiration threshold 620. A non-breathing interval 660 starts from the end of the expiration period 650 and continues until the beginning of a next inspiration period 670.

Detection of sleep apnea and severe sleep apnea is illustrated in FIG. 5. The patient's respiration signals are monitored and the respiration cycles are defined according to an inspiration 730, an expiration 750, and a non-breathing 760 interval as described in connection with FIG. 4. A condition of sleep apnea is detected when a non-breathing period 760 exceeds a first predetermined interval 790, denoted the sleep apnea interval. A condition of severe sleep apnea is detected when the non-breathing period 760 exceeds a second predetermined interval 795, denoted the severe sleep apnea interval. For example, sleep apnea may be detected when the non-breathing interval exceeds about 10 seconds, and severe sleep apnea may be detected when the non-breathing interval exceeds about 20 seconds.

Hypopnea is a condition of disordered breathing characterized by abnormally shallow breathing. Hypopnea reduces oxygen to the brain, and is linked with altered brain activity and brain states. The altered brain activity and brain states indicative of hypopnea may be used to activate or modify therapy in accordance with the present invention. FIG. 6 is a graph of tidal volume derived from transthoracic impedance measurements. The graph of FIG. 6 illustrating the tidal volume of a hypopnea episode may be compared to the tidal volume of a normal breathing cycle illustrated previously in FIG. 2, which illustrated normal respiration tidal volume and rate. As shown in FIG. 6, hypopnea involves a period of abnormally shallow respiration, possible at an increased respiration rate.

Hypopnea is detected by comparing a patient's respiratory tidal volume 803 to a hypopnea tidal volume 801. The tidal volume for each respiration cycle may be derived from transthoracic impedance measurements acquired in the manner described previously. The hypopnea tidal volume threshold may be established by, for example, using clinical results providing a representative tidal volume and duration of hypopnea events. In one configuration, hypopnea is detected when an average of the patient's respiratory tidal volume taken over a selected time interval falls below the hypopnea tidal volume threshold. Furthermore, various combinations of hypopnea cycles, breath intervals, and non-breathing intervals may be used to detect hypopnea, where the non-breathing intervals are determined as described above.

In FIG. 6, a hypopnea episode 805 is identified when the average tidal volume is significantly below the normal tidal volume. In the example illustrated in FIG. 6, the normal tidal volume during the breathing process is identified as the peak-to peak value identified as the respiratory tidal volume 803. The hypopnea tidal volume during the hypopnea episode 805 is identified as hypopnea tidal volume 801. For example, the hypopnea tidal volume 801 may be about 50% of the respiratory tidal volume 803. The value 50% is used by way of example only, and determination of thresholds for hypopnea events may be determined as any value appropriate for a given patient.

In the example above, if the tidal volume falls below 50% of the respiratory tidal volume 803, the breathing episode may be identified as a hypopnea event, originating the measurement of the hypopnea episode 805.

Figure 7:
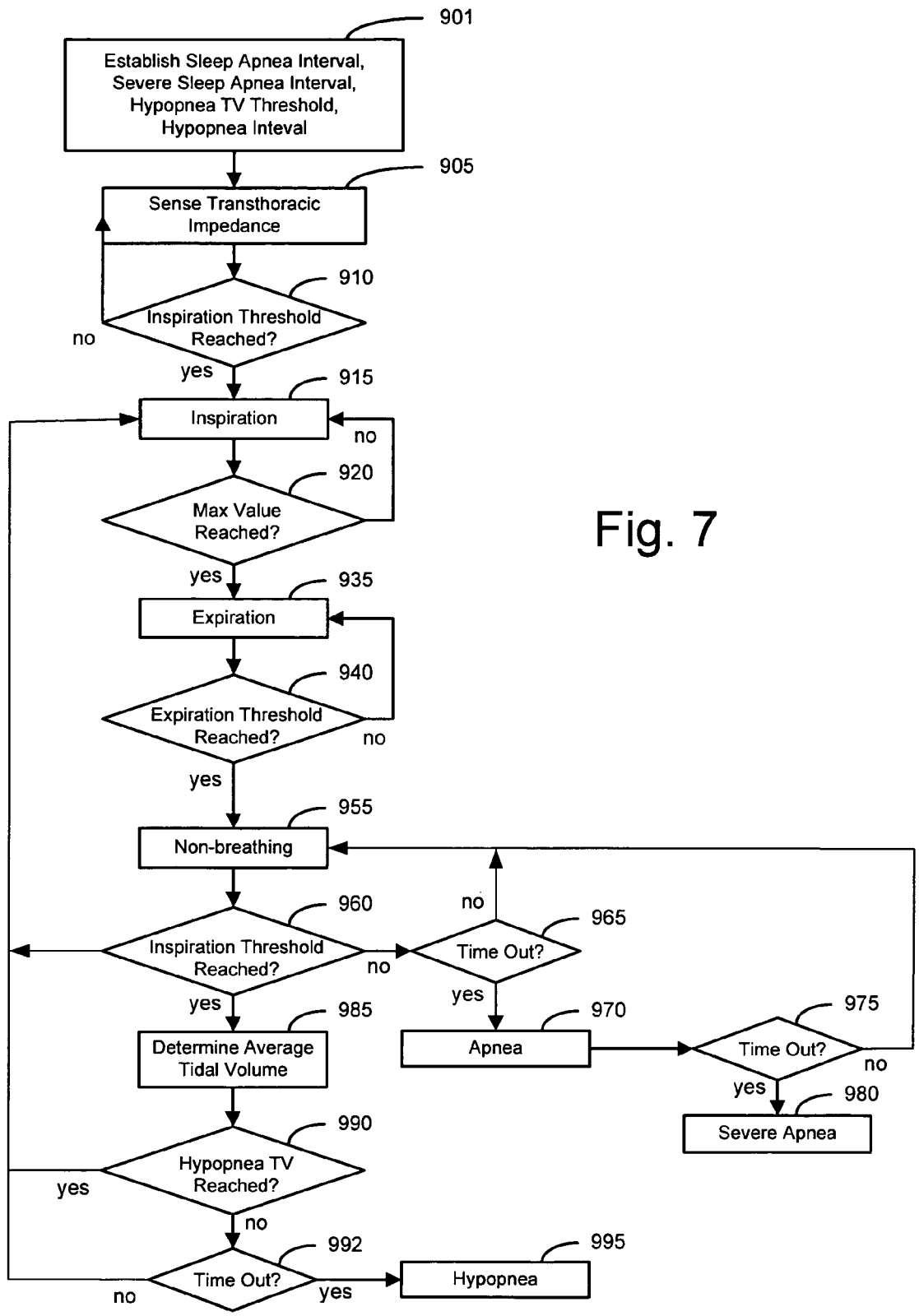
FIG. 7 is a flow chart illustrating a method of apnea and/or hypopnea detection according to embodiments of the invention.

FIG. 7 is a flow chart illustrating a method of apnea and/or hypopnea detection useful for activating, de-activating or modifying therapy based on brain activity in accordance with embodiments of the invention. Various parameters are established 901 before analyzing the patient's respiration for disordered breathing episodes, including, for example, inspiration and expiration thresholds, sleep apnea interval, severe sleep apnea interval, and hypopnea tidal volume (TV) threshold.

The patient's transthoracic impedance is measured 905 as described in more detail above. If the transthoracic impedance exceeds 910 the inspiration threshold, the beginning of an inspiration interval is detected 915. If the transthoracic impedance remains below 910 the inspiration threshold, then the impedance signal is checked 905 periodically until inspiration 915 occurs.

During the inspiration interval, the patient's transthoracic impedance is monitored until a maximum value of the transthoracic impedance is detected 920. Detection of the maximum value signals an end of the inspiration period and a beginning of an expiration period 935.

The expiration interval is characterized by decreasing transthoracic impedance. When, at determination 940, the transthoracic impedance falls below the expiration threshold, a non-breathing interval is detected 955.

If the transthoracic impedance determination 960 does not exceed the inspiration threshold within a first predetermined interval, denoted the sleep apnea interval 965, then a condition of sleep apnea is detected 970. Severe sleep apnea 980 is detected if the non-breathing period extends beyond a second predetermined interval, denoted the severe sleep apnea interval 975.

When the transthoracic impedance determination 960 exceeds the inspiration threshold, the tidal volume from the peak-to-peak transthoracic impedance is calculated, along with a moving average of past tidal volumes 985. The peak-to-peak transthoracic impedance provides a value proportional to the tidal volume of the respiration cycle. This value is compared at determination 990 to a hypopnea tidal volume threshold. If, at determination 990, the peak-to-peak transthoracic impedance is consistent with the hypopnea tidal volume threshold for a predetermined time 992, then a hypopnea cycle 995 is detected.

Figure 8:
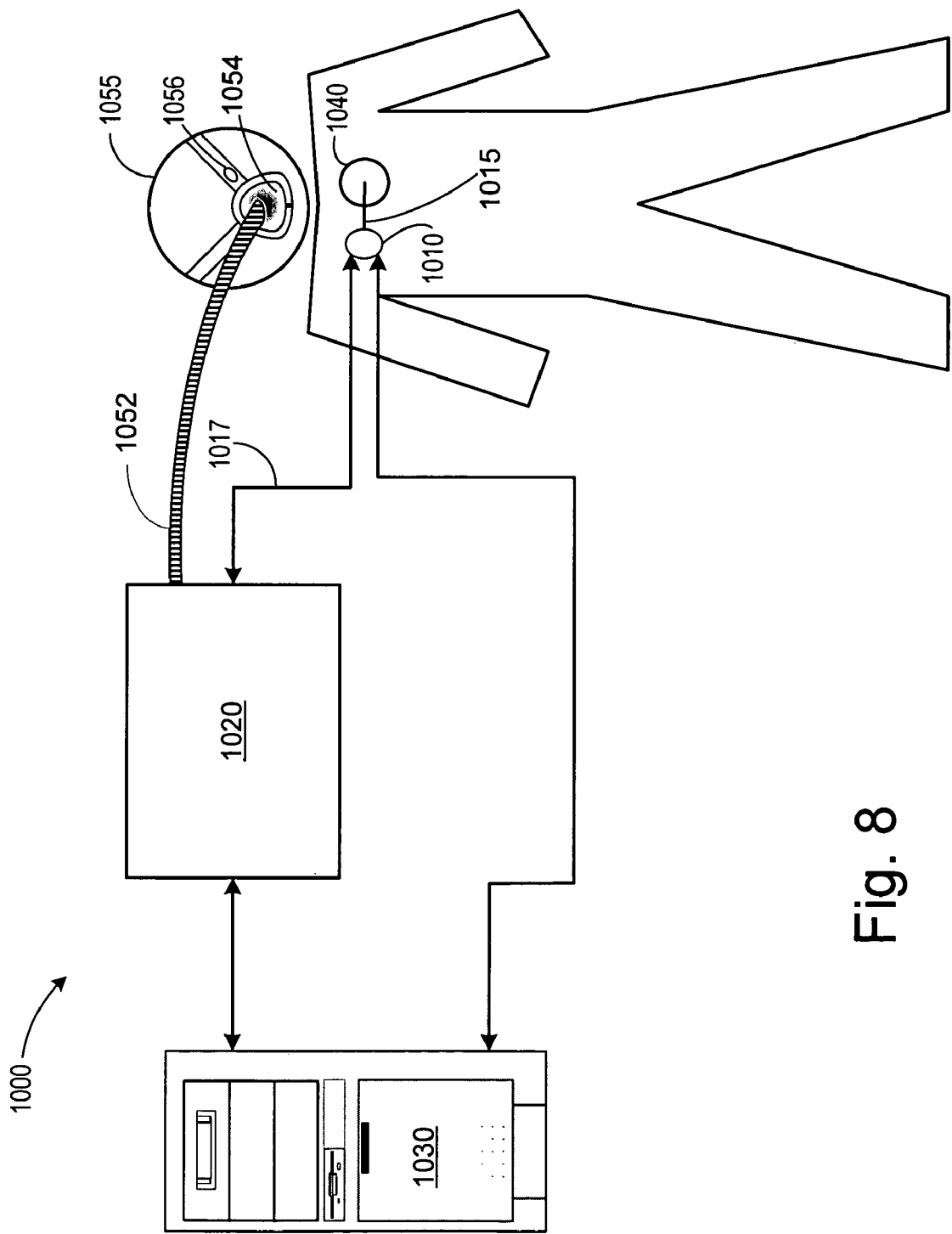
FIG. 8 illustrates a medical system including an implantable cardiac rhythm management device that cooperates with a patient-external respiration therapy device to provide coordinated patient monitoring, diagnosis and/or therapy using brain state information in accordance with an embodiment of the invention.

According to one embodiment of the invention, illustrated in FIG. 8, a medical system 1000 may include an implantable cardiac rhythm management device 1010 that cooperates with a patient-external respiration therapy device 1020 to provide coordinated patient monitoring, diagnosis and/or therapy. In the example illustrated in FIG. 8, a mechanical respiration therapy device, designated CPAP device 1020, includes a positive airway pressure device that cooperates with a CRM 1010. Positive airway pressure devices may be used to provide a variety of respiration therapies, including, for example, continuous positive airway pressure (CPAP), bi-level positive airway pressure (bi-level PAP), proportional positive airway pressure (PPAP), auto-titrating positive airway pressure, ventilation, gas or oxygen therapies. Such devices may also be configured to provide negative airway pressure on a selective basis as needed, such as in the treatment of Cheyne-Stokes breathing. These therapies may be activated, de-activated or adjusted based on brain state in accordance with the present invention.

The CPAP device 1020 develops a positive air pressure that is delivered to the patient's airway through a tube system 1052 and a mask 1054 connected to the CPAP device 1020. The mask 1054 may include EEG sensors, such as an EEG sensor 1056 attached to a strap 1057 that is placed around a head 1055 of the patient. Positive airway pressure devices are often used to treat disordered breathing. In one configuration, for example, the positive airway pressure provided by the CPAP device 1020 acts as a pneumatic splint keeping the patient's airway open and reducing the severity and/or number of occurrences of disordered breathing due to airway obstruction.

The CPAP device 1020 may directly control the delivery of respiration therapy to the patient, and may contribute to the control of the CRM device 1010. In addition, the CPAP device 1020 may provide a number of monitoring and/or diagnostic functions in relation to the respiratory system and/or other physiological systems.

The CRM 1010 and CPAP 1020 devices may communicate directly through a wireless communications link 1017, for example. Alternatively, or additionally, the CRM 1010 and CPAP 1020 devices may communicate with and/or through an APM such as an APM system 1030, as will be described further below with reference to FIG. 12. The CRM 1010 may be coupled to a heart 1040 of the patient using a lead system 1015, for example.

The CRM 1010 may provide a first set of monitoring, diagnostic, and/or therapeutic functions to a patient 1055. The CRM 1010 may be electrically coupled to a patient's heart 1040 through one or more cardiac electrodes 1015 terminating in, on, or about the heart 1040. The cardiac electrodes 1015 may sense cardiac signals produced by the heart 1040 and/or provide therapy to one or more heart chambers. For example, the cardiac electrodes 1015 may deliver electrical stimulation to one or more heart 1040 chambers, and/or to one or multiple sites within the heart 1040 chambers. The CRM 1010 may directly control delivery of one or more cardiac therapies, such as cardiac pacing, defibrillation, cardioversion, cardiac resynchronization, and/or other cardiac therapies, for example. In addition, the CRM 1010 may facilitate the control of a mechanical respiration device 1020. Further, the CRM 1010 may perform various monitoring and/or diagnostic functions in relation to the cardiovascular system and/or other physiological systems.

Although FIG. 8 illustrates a CRM device 1010 used with a CPAP device 1020 to provide coordinated patient monitoring, diagnosis and/or therapy, any number of patient-internal and patient-external medical devices may be included in a medical system in accordance with the invention. For example, a drug delivery device, such as a drug pump or controllable nebulizer, may be included in the system 1000. The drug delivery device may cooperate with either or both of the CRM device 1010 and the CPAP device 1020 and may contribute to the patient monitoring, diagnosis, and/or therapeutic functions of the medical system 1000.

Figure 9:
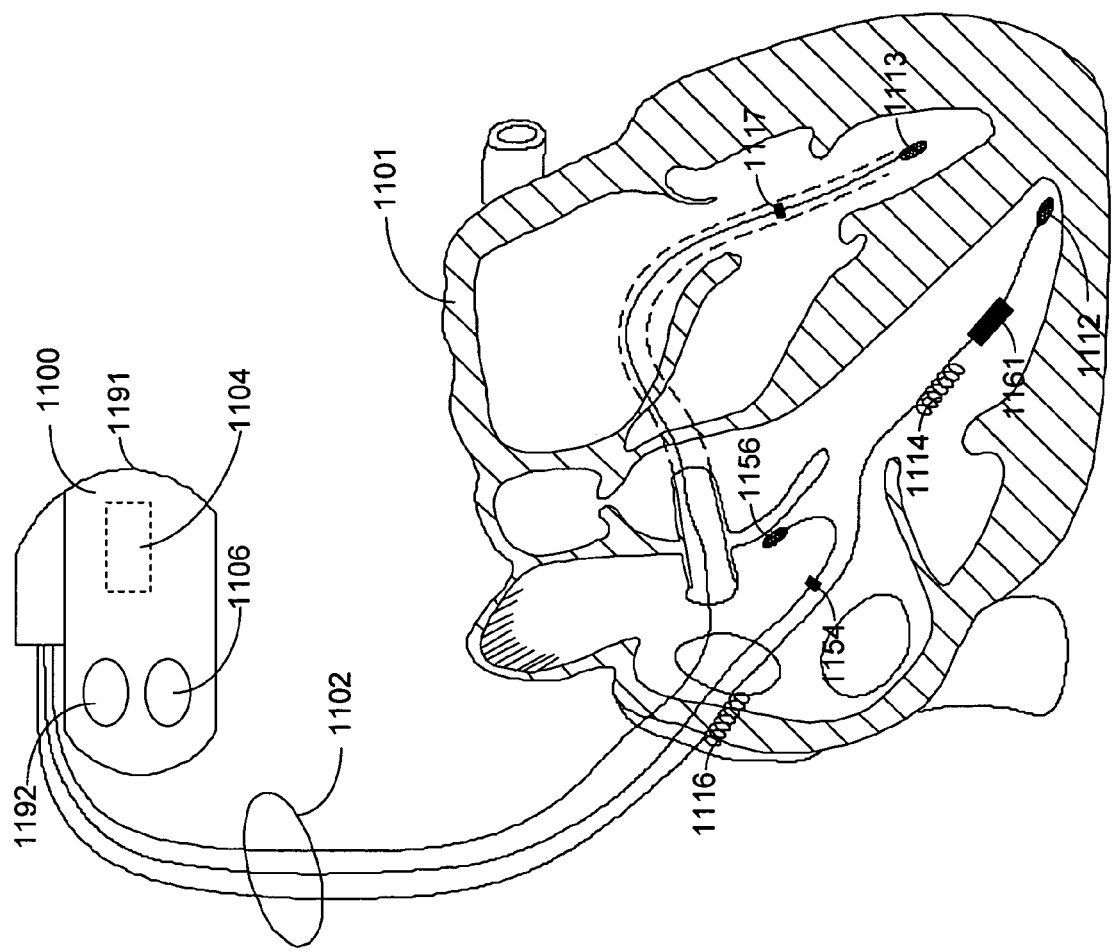
FIG. 9 is an illustration of an implantable cardiac device including a lead assembly shown implanted in a sectional view of a heart, the device used for coordinated patient monitoring, diagnosis, and/or therapy using brain state information in accordance with embodiments of the invention.

FIG. 9 is a partial view of an implantable CRM device that may include circuitry 1104 to activate, deactivate, or modify therapies based on brain state in accordance with embodiments of the invention. In this example, the implantable CRM device comprises an implantable pulse generator 1100 electrically and physically coupled to an intracardiac lead system 1102. Portions of the intracardiac lead system 1102 are inserted into the patient's heart 1101. The intracardiac lead system 1102 includes one or more electrodes configured to sense electrical cardiac activity of the heart, deliver electrical stimulation to the heart, sense the patient's transthoracic impedance, and/or sense other physiological parameters, e.g. cardiac chamber pressure or temperature. Portions of the housing 1191 of the pulse generator 1100 may optionally serve as a can electrode.

Communications circuitry is disposed within the housing 1191 for facilitating communication between the pulse generator 1100 and an external communication device, such as a portable or bed-side communication station, patient-carried/worn communication station, or external programmer, for example. The communications circuitry can also facilitate unidirectional or bidirectional communication with one or more implanted, external, cutaneous, or subcutaneous physiologic or non-physiologic sensors, patient-input devices and/or information systems.

The pulse generator 1100 may optionally incorporate movement sensor 1192 that may be used o implement rate adaptive pacing. The movement sensor 1192 may be implemented as an accelerometer positioned in or on the housing 1191 of the pulse generator 1100. If the movement sensor 1192 is implemented as an accelerometer, the movement sensor 1192 may also provide respiratory, e.g. snoring, rales, coughing, and cardiac, e.g. S1-S4 heart sounds, murmurs, and other acoustic information.

The lead system 1102 of the CRM device may incorporate one or more transthoracic impedance sensors that may be used to acquire the patient's respiration waveform, or other respiration-related information. The transthoracic impedance sensor may include, for example, one or more intracardiac electrodes 1116, 1114, 1154, 1156, 1112, 1117, 1113, 1161 positioned in one or more chambers of the heart 590. The intracardiac electrodes 1116, 1114, 1154, 1156, 1112, 1117, 1113, 1161 may be coupled to impedance drive/sense circuitry 1106 positioned within the housing 1191 of the pulse generator 1100.

In one implementation, impedance drive/sense circuitry 1106 generates a current that flows through the tissue between an impedance drive electrode 1154 and a can electrode on the housing 1191 of the pulse generator 1100. The voltage at an impedance sense electrode 1156 relative to the can electrode changes as the patient's transthoracic impedance changes. The voltage signal developed between the impedance sense electrode 1156 and the can electrode is detected by the impedance sense circuitry 1106. Other locations and/or combinations of impedance sense and drive electrodes are also possible.

The voltage signal developed at the impedance sense electrode 1156 is proportional to the patient's transthoracic impedance and represents the patient's respiration waveform. The transthoracic impedance increases during respiratory inspiration and decreases during respiratory expiration. The peak-to-peak transition of the transthoracic impedance is proportional to the amount of air moved in one breath, denoted the tidal volume. The amount of air moved per minute is denoted the minute ventilation. A normal "at rest" respiration pattern, e.g., during non-REM sleep, includes regular, rhythmic inspiration-expiration cycles without substantial interruptions.

The lead system 1102 may include one or more cardiac pace/sense electrodes 1154, 1156, 1112, 1117, 1113 positioned in, on, or about one or more heart chambers for sensing electrical signals from the patient's heart 1101 and/or delivering pacing pulses to the heart 1101. The intracardiac sense/pace electrodes 1154, 1156, 1112, 1117, 1113, such as those illustrated in FIG. 9, may be used to sense and/or pace one or more chambers of the heart, including the left ventricle, the right ventricle, the left atrium and/or the right atrium. The lead system 1102 may include one or more defibrillation electrodes 1116, 1114 for delivering defibrillation/cardioversion shocks to the heart.

The pulse generator 1100 may include circuitry for detecting cardiac arrhythmias and/or for controlling pacing or defibrillation therapy in the form of electrical stimulation pulses or shocks delivered to the heart through the lead system 1102. Circuitry 1104 for activating, deactivating, and/or modifying therapy based on brain state may be housed within the pulse generator 1100. The brain state activation circuitry 1104 may be coupled to various sensors, patient input devices, and/or other information systems through leads or through wireless communication links as described herein.

Figure 10:
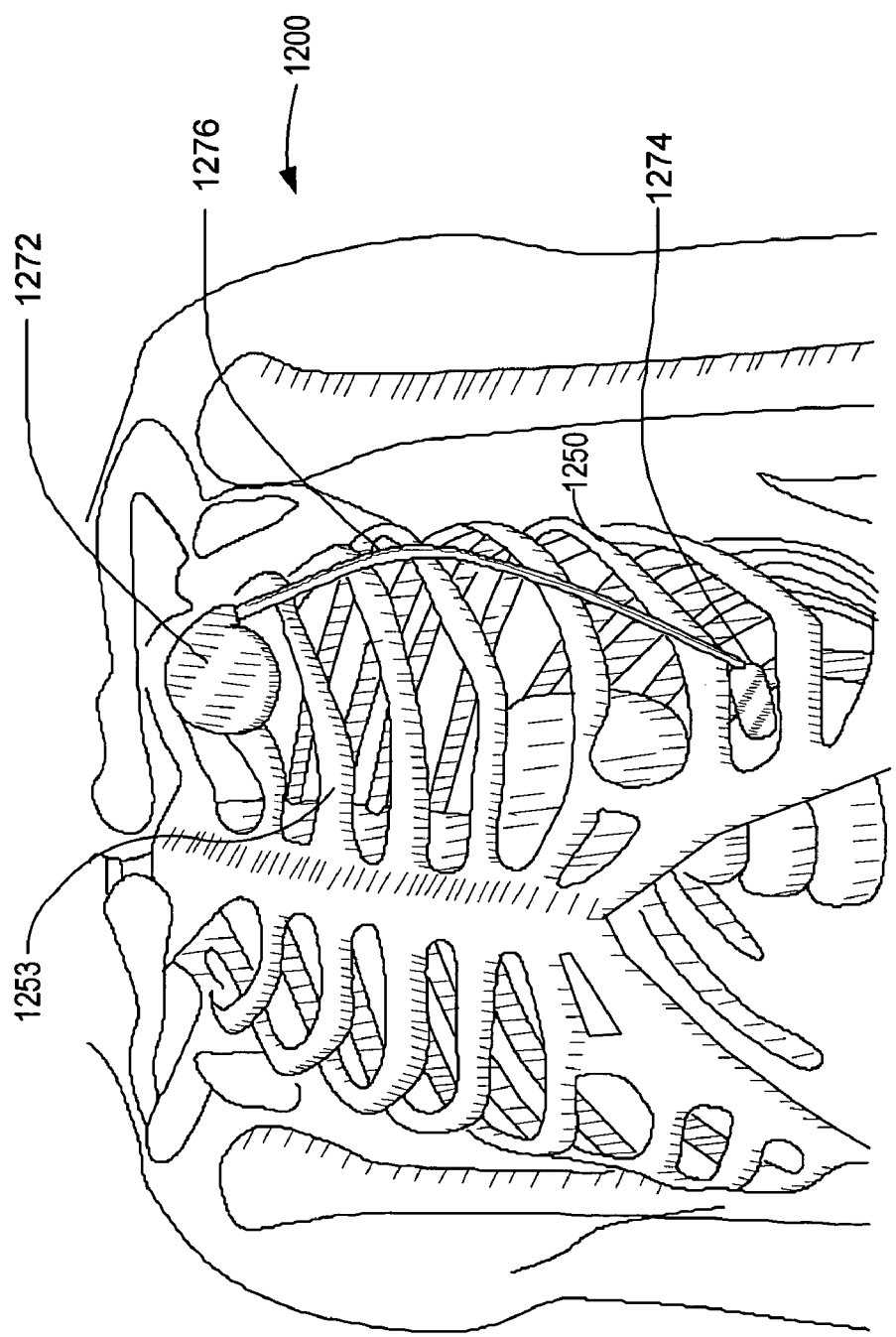
FIG. 10 is an illustration of a thorax having an implanted subcutaneous medical device that may be used for coordinated patient monitoring, diagnosis, and/or therapy using brain state information in accordance with an embodiment of the invention.

FIG. 10 is a diagram illustrating a subcutaneous implantable medical device 1200 that may be used for detecting brain state and activating, de-activating or modifying medical processes in accordance with embodiments of the invention. The device 1200 illustrated in FIG. 10 is an ITCS device that may be implanted under the skin in the chest region of a patient. The ITCS device may, for example, be implanted subcutaneously such that all or selected elements of the device are positioned on the patient's front, back, side, or other body locations suitable for sensing cardiac activity and delivering cardiac stimulation therapy. It is understood that elements of the ITCS device may be located at several different body locations, such as in the chest, abdominal, or subclavian region with electrode elements respectively positioned at different regions near, around, in, or on the heart.

The primary housing (e.g., the active or non-active can) of the ITCS device, for example, may be configured for positioning outside of a rib cage 1250 at an intercostal or subcostal location, within the abdomen, or in the upper chest region (e.g., subclavian location, such as above a third rib 1253). In one implementation, one or more electrodes may be located on a primary housing 1272 and/or at other locations about, but not in direct contact with the heart, great vessel or coronary vasculature.

In another implementation, one or more electrodes may be located in direct contact with the heart, great vessel or coronary vasculature, such as via one or more leads implanted by use of conventional transvenous delivery approaches. In another implementation, for example, one or more subcutaneous electrode subsystems or electrode arrays may be used to sense cardiac activity and deliver cardiac stimulation energy in an ITCS device configuration employing an active can or a configuration employing a non-active can. Electrodes may be situated at anterior and/or posterior locations relative to the heart.

In particular configurations, systems and methods may perform functions traditionally performed by pacemakers, such as providing various pacing therapies as are known in the art, in addition to cardioversion/defibrillation therapies. Exemplary pacemaker circuitry, structures and functionality, aspects of which may be incorporated in an ITCS device of a type that may benefit from multi-parameter sensing configurations, are disclosed in commonly owned U.S. Pat. Nos. 4,562,841; 5,284,136; 5,376,476; 5,036,849; 5,540,727; 5,836,987; 6,044,298; and 6,055,454, which are hereby incorporated herein by reference in their respective entireties. It is understood that ITCS device configurations may provide for non-physiologic pacing support in addition to, or to the exclusion of, bradycardia and/or anti-tachycardia pacing therapies.

An ITCS device in accordance with various embodiments may implement diagnostic and/or monitoring functions as well as provide cardiac stimulation therapy. Diagnostics functions may involve storing, trending, displaying, transmitting, and/or evaluating various indications based on the detection of EMG. Exemplary cardiac monitoring circuitry, structures and functionality, aspects of which may be incorporated in an ITCS of the invention, are disclosed in commonly owned U.S. Pat. Nos. 5,313,953; 5,388,578; and 5,411,031, which are hereby incorporated herein by reference in their respective entireties.

An ITCS device may be used to implement various diagnostic functions, which may involve performing rate-based, pattern and rate-based, and/or morphological tachyarrhythmia discrimination analyses. Subcutaneous, cutaneous, and/or external sensors, such as those previously described, may be employed to acquire physiologic and non-physiologic information for purposes of enhancing tachyarrhythmia detection and termination. It is understood that configurations, features, and combination of features described in the present disclosure may be implemented in a wide range of implantable medical devices, and that such embodiments and features are not limited to the particular devices described herein.

In FIG. 10, there is shown a configuration of a transthoracic cardiac sensing and/or stimulation (ITCS) device having components implanted in the chest region of a patient at different locations. In the particular configuration shown in FIG. 10, the ITCS device includes the housing 1272 within which various cardiac sensing, detection, processing, and energy delivery circuitry may be housed. It is understood that the components and functionality depicted in the figures and described herein may be implemented in hardware, software, or a combination of hardware and software. It is further understood that the components and functionality depicted as separate or discrete blocks/elements in the figures in general may be implemented in combination with other components and functionality, and that the depiction of such components and functionality in individual or integral form is for purposes of clarity of explanation, and not of limitation.

Communications circuitry may be disposed within the housing 1272 for facilitating communication between the ITCS device and an external communication device, such as a portable or bedside communication station, patient-carried/worn communication station, or external programmer, for example. The communications circuitry may also facilitate unidirectional or bidirectional communication with one or more external, cutaneous, or subcutaneous physiologic or non-physiologic sensors. The housing 1272 is typically configured to include one or more electrodes (e.g., can electrode and/or indifferent electrode). Although the housing 1272 is typically configured as an active can, it is appreciated that a non-active can configuration may be implemented, in which case at least two electrodes spaced apart from the housing 1272 are employed.

In the configuration shown in FIG. 10, a subcutaneous electrode 1274 may be positioned under the skin in the chest region and situated distal from the housing 1272. The subcutaneous and, if applicable, housing electrode(s) may be positioned about the heart at various locations and orientations, such as at various anterior and/or posterior locations relative to the heart. The subcutaneous electrode 1274 is coupled to circuitry within the housing 1272 via a lead assembly 1276. One or more conductors (e.g., coils or cables) are provided within the lead assembly 1276 and electrically couple the subcutaneous electrode 1274 with circuitry in the housing 1272. One or more sense, sense/pace or defibrillation electrodes may be situated on the elongated structure of the electrode support, the housing 1272, and/or the distal electrode assembly (shown as subcutaneous electrode 1274 in the configuration shown in FIG. 10).

In one configuration, the electrode support assembly and the housing 1272 define a unitary structure (e.g., a single housing/unit). The electronic components and electrode conductors/connectors are disposed within or on the unitary ITCS device housing/electrode support assembly. At least two electrodes are supported on the unitary structure near opposing ends of the housing/electrode support assembly. The unitary structure may have an arcuate or angled shape, for example.

According to another configuration, the electrode support assembly defines a physically separable unit relative to the housing 1272. The electrode support assembly includes mechanical and electrical couplings that facilitate mating engagement with corresponding mechanical and electrical couplings of the housing 1272. For example, a header block arrangement may be configured to include both electrical and mechanical couplings that provide for mechanical and electrical connections between the electrode support assembly and housing 1272. The header block arrangement may be provided on the housing 1272 or the electrode support assembly. Alternatively, a mechanical/electrical coupler may be used to establish mechanical and electrical connections between the electrode support assembly and housing 1272. In such a configuration, a variety of different electrode support assemblies of varying shapes, sizes, and electrode configurations may be made available for physically and electrically connecting to a standard ITCS device housing 1272.

Various embodiments described herein may be used in connection with subcutaneous monitoring, diagnosis, and/or therapy. Methods, structures, and/or techniques described herein relating to subcutaneous systems and methods may incorporate features of one or more of the following references: commonly owned U.S. patent application: "Subcutaneous Cardiac Sensing, Stimulation, Lead Delivery, and Electrode Fixation Systems and Methods," Ser. No. 60/462, 272, filed Apr. 11, 2003; U.S. Publication No. 2004/0215240; and U.S. Pat. No. 7,570,997, each hereby incorporated herein by reference.

Figure 11:
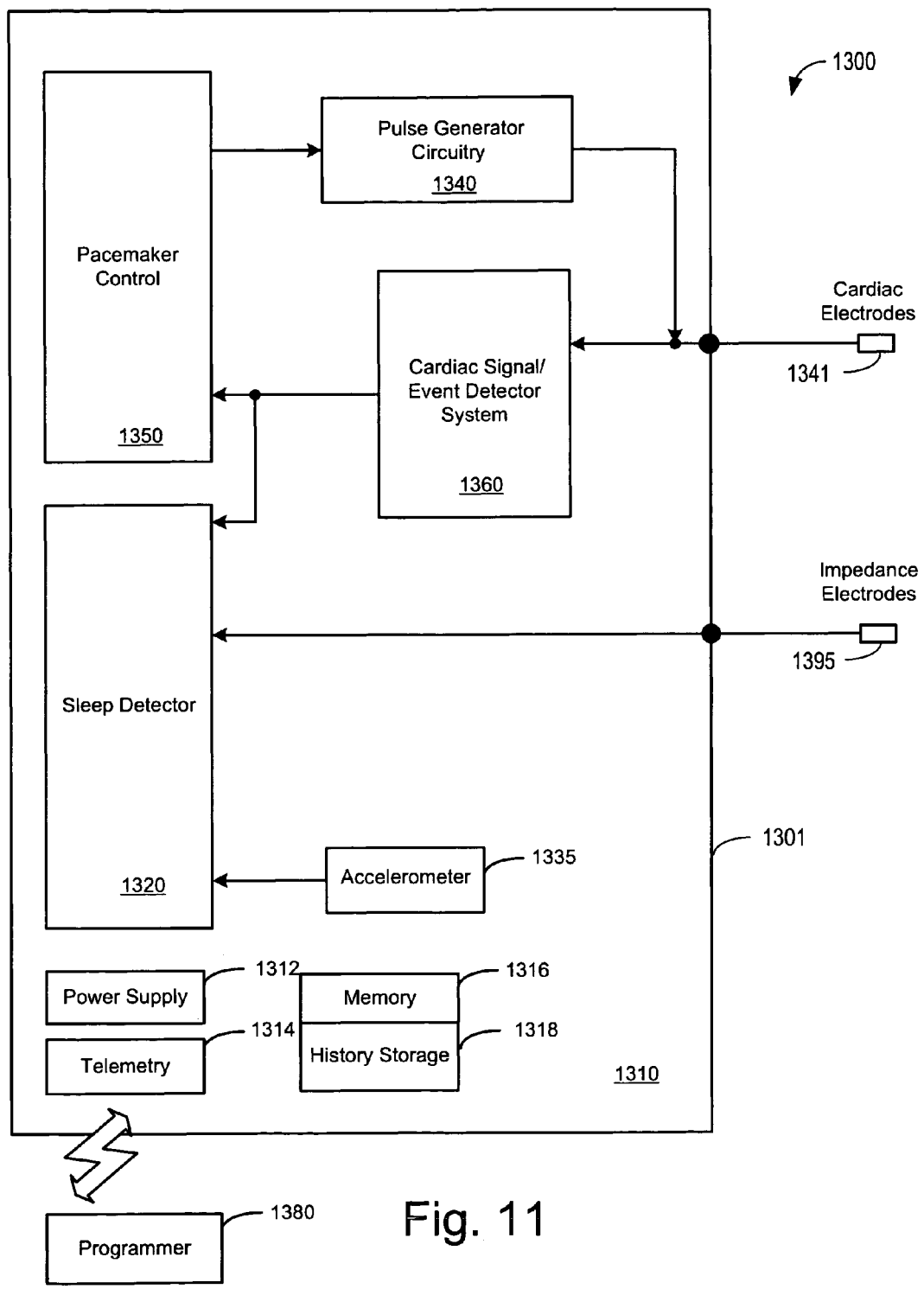
FIG. 11 is a block diagram of a cardiac rhythm management (CRM) system configured as a pacemaker and suitable for implementing a sleep detection methodology in accordance with embodiments of the invention.

Referring now to FIG. 11, there is shown a block diagram of an embodiment of a CRM system 1300 configured as a pacemaker and suitable for implantably detecting brain state and activating, de-activating or modifying medical processes in accordance with the invention. FIG. 11 shows the CRM 1300 divided into functional blocks. The CRM 1300 includes a sleep detector 1320 for receiving sleep-related signals and detecting sleep in accordance with embodiments of the invention.

In one embodiment, the sleep detector 1320 is incorporated as part of CRM circuitry 1310 encased and hermetically sealed in a housing 1301 suitable for implanting in a human body. Power to the CRM 1300 is supplied by an electrochemical battery power supply 1312 housed within the CRM 1300. A connector block (not shown) is additionally attached to the CRM 1300 to allow for the physical and electrical attachment of the cardiac lead system conductors to the CRM circuitry 1310.

The CRM circuitry 1310 may be configured as a programmable microprocessor-based system, with circuitry for detecting sleep in addition to providing pacing therapy to the heart. Cardiac signals sensed by one or more cardiac electrodes 1341 may be processed by the cardiac event detection circuitry 1360. Pace pulses controlled by the pacemaker control 1350 and generated by the pulse generator 1340 are delivered to the heart to treat various arrhythmias of the heart.

The memory circuit 1316 may store parameters for various device operations involved in sleep detection and/or cardiac pacing and sensing. The memory circuit 1316 may also store data indicative of sleep-related signals received by components of the CRM circuitry 1310, such as information derived from one or more impedance electrodes 1395, the cardiac signal detector system 1360, the accelerometer 1335, and/or the sleep detector 1320.

As illustrated in FIG. 11, the sleep detector 1320 receives signals derived from the cardiac event detector 1360, the impedance electrodes 1395 and the accelerometer 1335 to perform operations involving detecting sleep onset and sleep termination according to the principles of the invention. Historical data storage 1318 may be coupled to the sleep detection circuitry 1320 for storing historical sleep related data. Such data may be transmitted to an external programmer unit 1380 and used for various diagnostic purposes and as needed or desired.

Telemetry circuitry 1314 is coupled to the CRM circuitry 1310 to allow the CRM 1300 to communicate with a remote device such as the programmer 1380, or other device such as a patient-external EEG sensor. In one embodiment, the telemetry circuitry 1314 and the programmer 1380 use a wire loop antenna and a radio frequency telemetric link to receive and transmit signals and data between the programmer 1380 and telemetry circuitry 1314. In this manner, programming commands and data (such as EEG data) may be transferred between the CRM circuitry 1310 and the one or more remote devices 1380 during and after implant.

The programming commands allow a physician to set or modify various parameters used by the CRM system 1300. These parameters may include setting sleep detection parameters for use during sleep detection, such as which sleep-related signals are to be used for sleep detection and threshold adjustment, and the initial sleep detection thresholds. In addition, the CRM system 1300 may download to the programmer 1380 stored data pertaining to sensed sleep periods, including the amount of time spent sleeping, the time of day sleep periods occurred, historical data of sleep times, and the number of arousals during the sleep periods, for example.

Still referring to FIG. 11, signals associated with patient activity, indicative of brain state, may be detected through the use of an accelerometer 1335 positioned within the housing 1301 of the CRM 1300. The accelerometer 1335 may be responsive to patient activity. The accelerometer signal may be correlated with activity level or workload, for example. Signals derived from the accelerometer 1335 are coupled to the sleep detector 1320 and may also be used by the pacemaker 1350 for implementing a rate adaptive pacing regimen, for example.

The impedance electrodes 1395 sense the patient's transthoracic impedance. As described earlier, transthoracic impedance may also be useful as an indirect measure of brain state. The transthoracic impedance may be used to calculate various parameters associated with respiration. Impedance driver circuitry (not shown) induces a current that flows through the blood between the impedance drive electrode and a can electrode on the housing 1301 of the CRM 1300. The voltage at an impedance sense electrode relative to the can electrode changes as the transthoracic impedance changes. The voltage signal developed between the impedance sense electrode and the can electrode is detected by the impedance sense amplifier and is delivered to the sleep detector circuitry 1320 for further processing.

Figure 12:
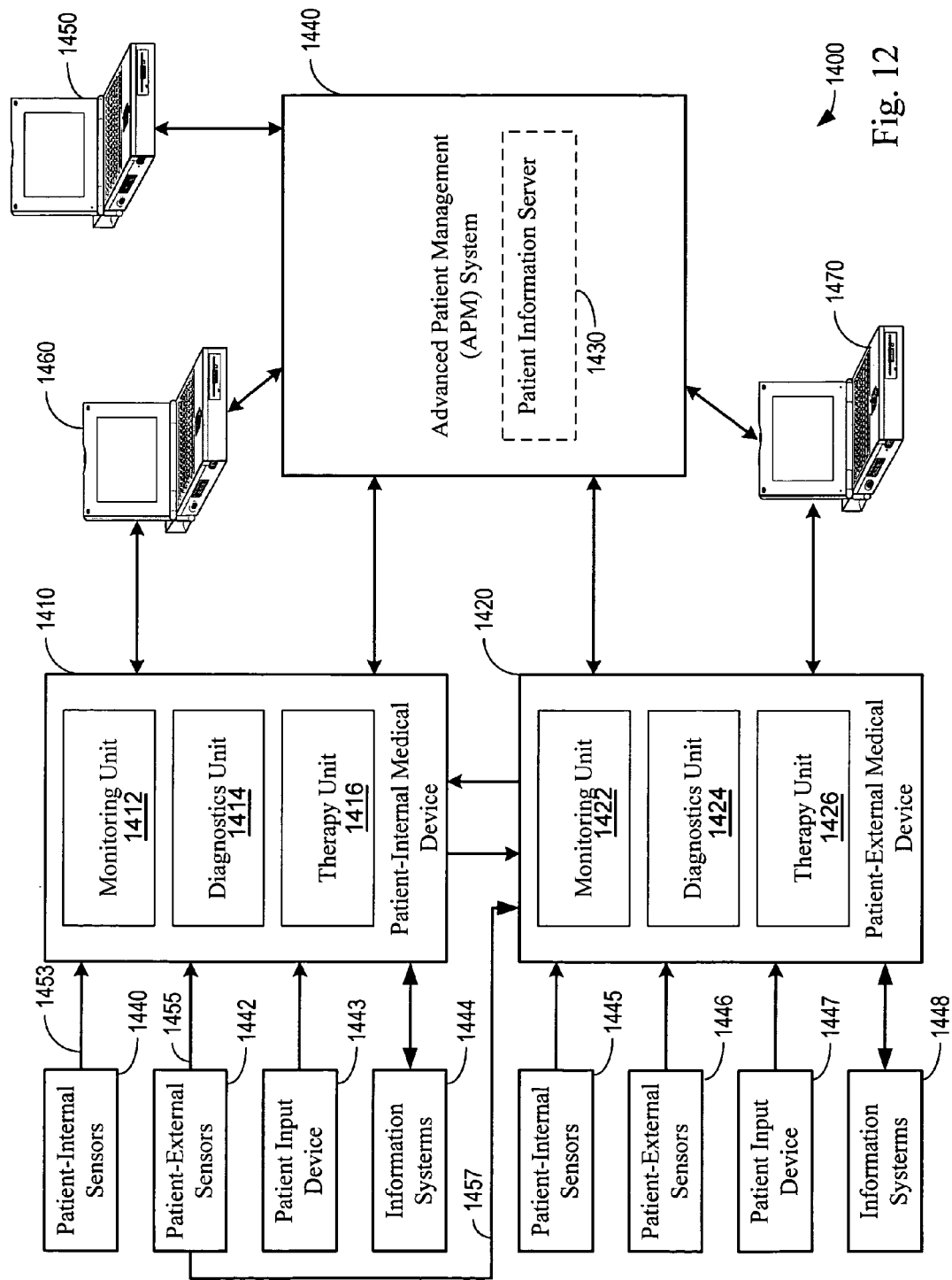
FIG. 12 is a block diagram of a medical system that may be used to implement coordinated patient monitoring, diagnosis, and/or therapy using brain state information in accordance with embodiments of the invention.

FIG. 12 is a block diagram of a medical system 1400 that may be used to implement coordinated patient measuring and/or monitoring, diagnosis, and/or therapy, including detecting EEG's and determining the brain state in accordance with embodiments of the invention. The medical system 1400 may include, for example, one or more patient-internal medical devices 1410 and one or more patient-external medical devices 1420. Each of the patient-internal 1410 and patient-external 1420 medical devices may include one or more of a patient monitoring unit 1412, 1422, a diagnostics unit 1414, 1424, and/or a therapy unit 1416, 1426.

The patient-internal medical device 1410 is typically a fully or partially implantable device that performs measuring, monitoring, diagnosis, and/or therapy functions. The patient-external medical device 1420 performs monitoring, diagnosis and/or therapy functions external to the patient (i.e., not invasively implanted within the patient's body). The patient-external medical device 1420 may be positioned on the patient, near the patient, or in any location external to the patient. It is understood that a portion of a patient-external medical device 1420 may be positioned within an orifice of the body, such as the nasal cavity or mouth, yet may be considered external to the patient (e.g., mouth pieces/appliances, tubes/appliances for nostrils, or temperature sensors positioned in the ear canal).

The patient-internal and patient-external medical devices 1410, 1420 may be coupled to one or more sensors 1441, 1442, 1445, 1446, patient input devices 1443, 1447 and/or other information acquisition devices 1444, 1448. The sensors 1441, 1442, 1445, 1446, patient input devices 1443, 1447, and/or other information acquisition devices 1444, 1448 may be employed to detect conditions relevant to the monitoring, diagnostic, and/or therapeutic functions of the patient-internal and patient-external medical devices 1410, 1420.

The medical devices 1410, 1420 may each be coupled to one or more patient-internal sensors 1441, 1445 that are fully or partially implantable within the patient. The medical devices 1410, 1420 may also be coupled to patient-external sensors positioned on, near, or in a remote location with respect to the patient. For example, the patient-external sensors 1442 may include EEG sensors useful for detecting brain activity. The patient-internal and patient-external sensors may also be used to sense conditions, such as physiological or environmental conditions, that affect the patient.

The patient-internal sensors 1441 may be coupled to the patient-internal medical device 1410 through one or more internal leads 1453. In one example, as was described above with reference to FIG. 9, an internal endocardial lead system is used to couple cardiac electrodes to an implantable pacemaker or other cardiac rhythm management device. Still referring to FIG. 12, one or more patient-internal sensors 1441 may be equipped with transceiver circuitry to support wireless communications between the one or more patient-internal sensors 1441 and the patient-internal medical device 1410 and/or the patient-external medical device 1420.

The patient-external sensors 1442 may be coupled to the patient-internal medical device 1410 and/or the patient-external medical device 1420 through one or more internal leads 1455 or through wireless connections. Patient-external sensors 1442 may communicate with the patient-internal medical device 1410 wirelessly. Patient-external sensors 1446 may be coupled to the patient-external medical device 1420 through one or more internal leads 1457 or through a wireless link.

The medical devices 1410, 1420 may be coupled to one or more patient input devices 1443, 1447. The patient input devices are used to allow the patient to manually transfer information to the medical devices 1410, 1420. The patient input devices 1443, 1447 may be particularly useful for inputting information concerning patient perceptions, such as how well the patient feels, and information such as patient smoking, drug use, or other activities that are not automatically sensed or detected by the medical devices 1410, 1420.

The medical devices 1410, 1420 may be connected to one or more information acquisition devices 1444, 1448, for example, a database that stores information useful in connection with the monitoring, diagnostic, or therapy functions of the medical devices 1410, 1420. For example, one or more of the medical devices 1410, 1420 may be coupled through a network to a patient information server 1430 that provides information about environmental conditions affecting the patient, e.g., the pollution index for the patient's location.

In one embodiment, the patient-internal medical device 1410 and the patient-external medical device 1420 may communicate through a wireless link between the medical devices 1410, 1420. For example, the patient-internal and patient-external devices 1410, 1420 may be coupled through a short-range radio link, such as Bluetooth, IEEE 802.11, and/or a proprietary wireless protocol. The communications link may facilitate unidirectional or bidirectional communication between the patient-internal 1410 and patient-external 1420 medical devices. Data and/or control signals may be transmitted between the patient-internal 1410 and patient-external 1420 medical devices to coordinate the functions of the medical devices 1410, 1420.

In another embodiment, the patient-internal and patient-external medical devices 1410, 1420 may be used within the structure of an advanced patient management system 1440. Advanced patient management systems 1440 involve a system of medical devices that are accessible through various communications technologies. For example, patient data may be downloaded from one or more of the medical devices periodically or on command, and stored at the patient information server 1430. The physician and/or the patient may communicate with the medical devices and the patient information server 1430, for example, to acquire patient data or to initiate, terminate or modify therapy.

The data stored on the patient information server 1430 may be accessible by the patient and the patient's physician through one or more terminals 1450, e.g., remote computers located in the patient's home or the physician's office. The patient information server 1430 may be used to communicate to one or more of the patient-internal and patient-external medical devices 1410, 1420 to provide remote control of the monitoring, diagnosis, and/or therapy functions of the medical devices 1410, 1420.

In one embodiment, the patient's physician may access patient data transmitted from the medical devices 1410, 1420 to the patient information server 1430. After evaluation of the patient data, the patient's physician may communicate with one or more of the patient-internal or patient-external devices 1410, 1420 through the APM system 1440 to initiate, terminate, or modify the monitoring, diagnostic, and/or therapy functions of the patient-internal and/or patient-external medical systems 1410, 1420. Systems and methods involving advanced patient management techniques are further described in U.S. Pat. Nos. 6,336,903, 6,312,378, 6,270,457, and 6,398,728, hereby incorporated herein by reference.

In another embodiment, the patient-internal and patient-external medical devices 1410, 1420 may not communicate directly, but may communicate indirectly through the APM system 1440. In this embodiment, the APM system 1440 may operate as an intermediary between two or more of the medical devices 1410, 1420. For example, data and/or control information may be transferred from one of the medical devices 1410, 1420 to the APM system 1440. The APM system 1440 may transfer the data and/or control information to another of the medical devices 1410, 1420.

In one embodiment, the APM system 1440 may communicate directly with the patient-internal and/or patient-external medical devices 1410, 1420. In another embodiment, the APM system 1440 may communicate with the patient-internal and/or patient-external medical devices 1410, 1420 through medical device programmers 1460, 1470 respectively associated with each medical device 1410, 1420.

Various embodiments described herein may be used in connection with advanced patient management. Methods, structures, and/or techniques described herein relating to advanced patient management, such as those involving remote patient/device monitoring, diagnosis, therapy, or other advanced patient management related methodologies, may incorporate features of one or more of the following references: U.S. Pat. Nos. 6,221,011; 6,277,072; 6,280,380; 6,358,203; 6,368,284; and 6,440,066 each hereby incorporated herein by reference.

A number of the examples presented herein involve block diagrams illustrating functional blocks used for coordinated monitoring, diagnosis and/or therapy functions in accordance with embodiments of the invention. It will be understood by those skilled in the art that there exist many possible configurations in which these functional blocks may be arranged and implemented. The examples depicted herein provide examples of possible functional arrangements used to implement the approaches of the invention.

Each feature disclosed in this specification (including any accompanying claims, abstract, and drawings), may be replaced by alternative features having the same, equivalent or similar purpose, unless expressly stated otherwise. Thus, unless expressly stated otherwise, each feature disclosed is one example only of a generic series of equivalent or similar features.

Various modifications and additions can be made to the embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A system, comprising:
a housing configured to be implanted;
a sensor system having one or more sensors configured to sense brain activity;
a brain activity detector coupled to the sensor system and configured to determine a brain state based on signals received from the sensor system;
a medical system comprising a cardiac rhythm management device and configured to perform at least one respiratory or cardiac process; and
a controller coupled to the brain activity detector and the medical system, the controller configured to execute program instruction stored in memory to cause the medical system to activate, de-activate or adjust the at least one cardiac or respiratory process based on the brain state, including executing stored instructions to modify a cardiac rhythm management therapy to address cardiac rhythm disturbances associated with an abnormal brain state based on identification of the abnormal brain state by at least one of the controller and the brain activity detector, wherein at least one of the sensor system and the controller are at least partially housed within the housing.

2. The system of claim 1, wherein the sensor system comprises at least one EEG sensor and the brain activity detector is configured to execute stored program instructions to determine the brain state based on EEG signals sensed by the EEG sensor.

3. The system of claim 1, wherein the sensor system comprises at least one EEG sensor and at least one EMG sensor, and the brain activity detector is configured to execute stored program instruction to determine the brain state based on EEG signals and EMG signals.

4. The system of claim 1, wherein at least one of the brain activity detector and the controller is configured to execute stored program instructions to determine relative sleep deepness, and the controller is configured to execute stored program instructions to decrease intensity of a sleep-disordered breathing therapy delivered by the medical system based on detection of a deeper level of sleep relative to a lighter level of sleep.

5. The system of claim 4, wherein at least one of the brain activity detector and the controller is configured to execute stored program instructions to identify at least REM sleep, sleep stage 3, and sleep state 4, and the controller is configured to execute stored program instructions to at least one of decrease and terminate the sleep-disordered breathing therapy based on detection of at least one of sleep stage 3, sleep stage 4, and sleep stage 4.

6. The system of claim 1, wherein the medical system comprises an external respiratory therapy device configured to deliver a disordered breathing therapy.

7. The system of claim 1, wherein the sensor system is housed within the housing and configured to sense EEG signals.

8. The system of claim 1, wherein the cardiac rhythm management device is configured to deliver a sleep-disordered breathing therapy comprising cardiac stimulation pulses and the controller is configured to execute stored program instruction to activate, de-activate, or adjust the sleep-disordered breathing therapy delivered by the medical system based on the brain state.

9. The system of claim 1, wherein the medical system further comprises an external respiratory therapy device, the controller is disposed in the cardiac rhythm management circuitry device or the external respiratory therapy device, and the controller is configured to execute stored program instructions to control at least one therapy function for each of the cardiac rhythm management device and the external respiratory therapy device.

10. The system of claim 1, wherein the sensor system is configured to sense impedance signals and the brain activity detector is configured execute program instructions to determine the brain state using the impedance signals.

11. The system of claim 1, wherein the housing further houses cardiac pacing circuitry configured to deliver a cardiac pacing therapy, at least one of the brain activity detector and the controller is configured to execute stored program instructions to identify proarrhythmic sleep periods, and the controller is configured to execute stored program instructions to cause the cardiac pacing circuitry to deliver atrial overdrive pacing during identified proarrhythmic sleep periods.

12. A method, comprising:
sensing signals indicative of brain activity, including sensing signals indicative of seizure;
determining a brain state of a patient based on the sensed signals; and
controlling at least one of a respiratory or a cardiac medical process based on brain state, including activating, de-activating or adjusting arrhythmia therapy based on the signals indicative of seizure, wherein at least one of sensing, determining, and controlling are performed by implanted components.

13. The method of claim 12, wherein sensing the signals indicative of brain state comprises sensing EEG signals and controlling the at least one of the respiratory process or the cardiac medical process comprises controlling at least one of a cardiac pacing therapy or a xPAP therapy.

14. The method of claim 12, wherein:
sensing signals related to brain state comprises determining a sleep stage of the patient; and
controlling the at least one medical process comprises activating, de-activating or adjusting a sleep disordered breathing therapy based on the patient's sleep stage.

15. The method of claim 12, wherein sensing signals comprises sensing at least one EMG signal to detect an effect of neural stimulation.

16. The method of claim 12, wherein sensing signals comprises sensing EEG signals and controlling the at least one medical process comprises activating, de-activating or adjusting a respiratory therapy delivered by an implantable cardiac pacing device.

17. The method of claim 12, wherein controlling the at least one medical process comprises activating, de-activating or adjusting a cardiac pacing therapy.

18. A system, comprising:
a housing configured to be implanted;
a sensor system having one or more sensors configured to sense brain activity;
a brain activity detector coupled to the sensor system and configured to determine a brain state based on signals received from the sensor system;
a medical system comprising an implantable cardiac rhythm management device configured to deliver a sleep-disordered breathing therapy comprising cardiac stimulation pulses; and
a controller coupled to the brain activity detector and the medical system, the controller configured to execute program instruction stored in memory to cause the medical system to activate, de-activate or adjust the sleep-disordered breathing therapy delivered by the medical system based on the brain state, wherein at least one of the sensor system and the controller are at least partially housed within the housing.

19. A system, comprising:
a housing configured to be implanted;
a sensor system having one or more sensors configured to sense brain activity;
a brain activity detector coupled to the sensor system and configured to determine a brain state based on signals received from the sensor system;
a medical system comprising a cardiac rhythm management device and an external respiratory therapy device configured to perform at least one respiratory or cardiac process; and
a controller coupled to the brain activity detector and the medical system, the controller configured to execute program instruction stored in memory to cause the medical system to control at least one therapy function for each of the cardiac rhythm management device and the external respiratory therapy device, wherein the controller is disposed in the cardiac rhythm management circuitry device or the external respiratory therapy device.

20. A system, comprising:
a housing configured to be implanted;
a sensor system having one or more sensors configured to sense brain activity;
a brain activity detector coupled to the sensor system and configured to determine a brain state based on signals received from the sensor system;
a medical system comprising cardiac pacing circuitry disposed in the housing configured to deliver a cardiac pacing therapy; and
a controller coupled to the brain activity detector and the medical system, the controller configured to execute program instruction stored in memory to cause the medical system to activate, de-activate or adjust the at least one cardiac or respiratory process based on the brain state, wherein at least one of the brain activity detector and the controller is configured to execute stored program instructions to identify proarrhythmic sleep periods and the controller is configured to execute stored program instructions to cause the cardiac pacing circuitry to deliver atrial overdrive pacing during identified proarrhythmic sleep periods and wherein at least one of the sensor system and the controller are at least partially housed within the housing.

* * * * *

UNITED STATES PATENT AND TRADEMARK OFFICE
CERTIFICATE OF CORRECTION

PATENT NO. : 7,668,591 B2  Page 1 of 1
APPLICATION NO. : 10/922663
DATED : February 23, 2010
INVENTOR(S) : Lee et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1492 days.

Signed and Sealed this

Twenty-eighth Day of December, 2010

David J. Kappos
*Director of the United States Patent and Trademark Office*